United States Patent
Sunaga et al.

(10) Patent No.: US 9,070,212 B2
(45) Date of Patent: Jun. 30, 2015

(54) MEDICAL IMAGING APPARATUS AND IMAGING SLICE DETERMINATION METHOD

(75) Inventors: Kentaro Sunaga, Tokyo (JP); Atsushi Shiromaru, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 100 days.

(21) Appl. No.: 13/808,128

(22) PCT Filed: Jun. 28, 2011

(86) PCT No.: PCT/JP2011/064738
§ 371 (c)(1),
(2), (4) Date: Jan. 3, 2013

(87) PCT Pub. No.: WO2012/008296
PCT Pub. Date: Jan. 19, 2012

(65) Prior Publication Data
US 2013/0106905 A1 May 2, 2013

(30) Foreign Application Priority Data
Jul. 15, 2010 (JP) ................................ 2010-160710

(51) Int. Cl.
G06K 9/00 (2006.01)
G06T 11/00 (2006.01)
A61B 5/055 (2006.01)
A61B 5/00 (2006.01)
A61B 6/00 (2006.01)

(52) U.S. Cl.
CPC ............... G06T 11/003 (2013.01); A61B 5/055 (2013.01); A61B 5/7425 (2013.01); A61B 5/743 (2013.01); A61B 5/7435 (2013.01); A61B 5/744 (2013.01)

(58) Field of Classification Search
USPC ......... 382/100, 103, 128–134, 154, 162, 168, 382/172, 181, 189, 224, 232, 254, 274, 276, 382/287, 305, 312; 345/619; 324/309, 307; 378/4, 21
See application file for complete search history.

(56) References Cited

U.S. PATENT DOCUMENTS 6,995,559 B2* 2/2006 Agilandam et al. .......... 324/309
7,403,004 B2* 7/2008 Morich et al. ................ 324/309

(Continued)

FOREIGN PATENT DOCUMENTS

JP 2005-125099 5/2005
JP 2009-279218 12/2009

OTHER PUBLICATIONS

International Search Report in corresponding PCT/JP2011/064738.

(Continued)

Primary Examiner — Seyed Azarian
(74) Attorney, Agent, or Firm — Cooper & Dunham LLP

(57) ABSTRACT

There is provided an imaging slice setting technique capable of reducing the burden on the operator and having high accuracy and a high degree of freedom. In order to do so, a standard imaging slice is registered in the system in advance, and a GUI allowing the operator to appropriately adjust the standard imaging slice is provided. The standard imaging slice is displayed on a standard image configured to include two-dimensional images in three directions similar to a positioning image, and can be adjusted on the image. At the time of main imaging, the standard image is fitted to the positioning image to specify an imaging slice on the positioning image.

9 Claims, 16 Drawing Sheets

(56) References Cited

U.S. PATENT DOCUMENTS

| | | | |
|---|---|---|---|
| 8,334,878 B2* | 12/2012 | Moriya et al. | 345/619 |
| 2005/0088177 A1* | 4/2005 | Schreck et al. | 324/307 |
| 2006/0233430 A1* | 10/2006 | Kimura | 382/128 |

OTHER PUBLICATIONS

Feb. 17, 2015 Japanese official action in corresponding Japanese Patent Application No. 2012-524512.

* cited by examiner

FIG. 4

| EXAMINATION PART | STANDARD IMAGE | EXAMINATION SECTION | STANDARD IMAGING SLICE POSITION INFORMATION | OPERATION SECTION | OPERATING POINT POSITION INFORMATION |
|---|---|---|---|---|---|
| | | | | | |
| | | | | | |
| | | | | | |

310, 320, 330, 340, 350, 360 — 722

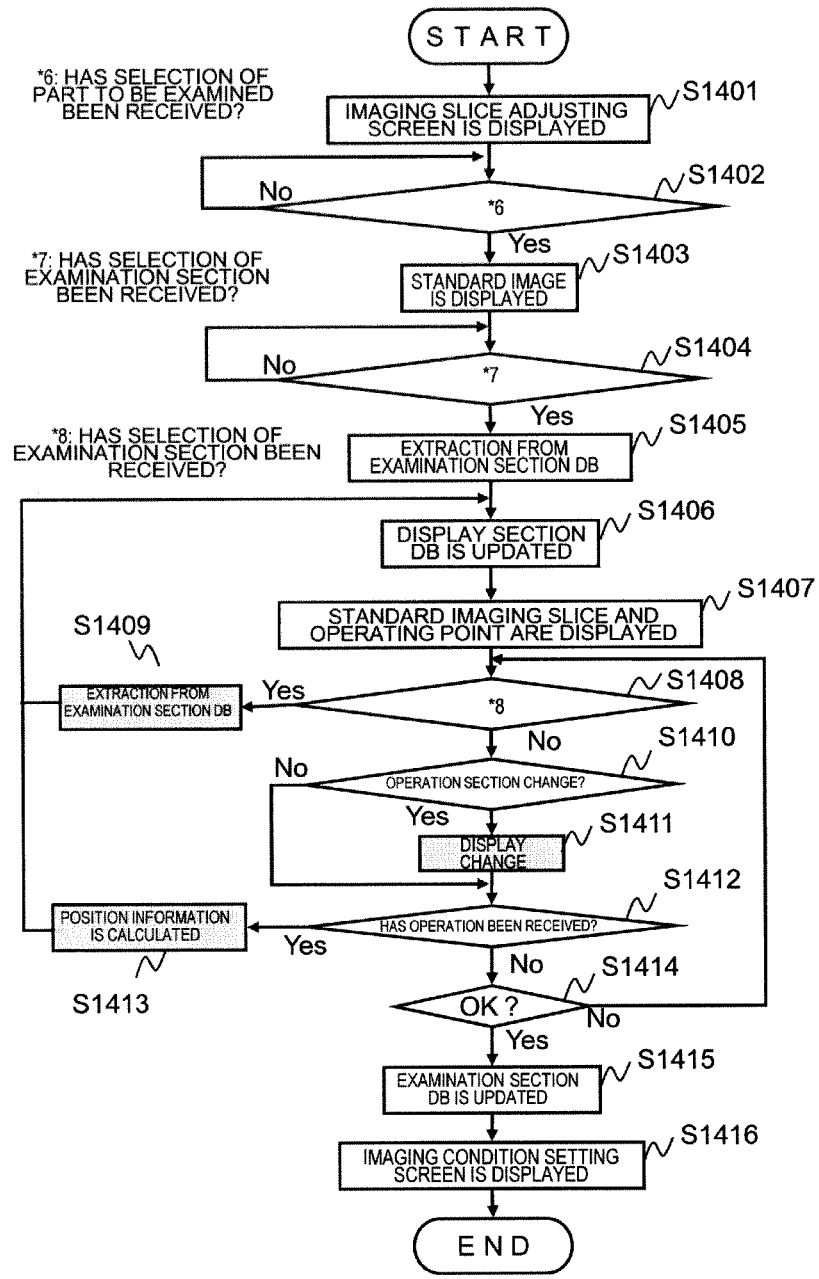

MEDICAL IMAGING APPARATUS AND IMAGING SLICE DETERMINATION METHOD

TECHNICAL FIELD

The present invention relates to a technique for assisting an imaging position setting in a medical imaging apparatus.

BACKGROUND ART

A magnetic resonance imaging (hereinafter, referred to as "MRI") apparatus, which is an example of a medical imaging apparatus, is an apparatus that measures a nuclear magnetic resonance (hereinafter, referred to as "NMR") signal generated by an object, especially the spin of nuclei that form human tissue, and images the shapes or functions of the head, abdomen, limbs, and the like in a two-dimensional manner or in a three-dimensional manner. Different phase encoding and different frequency encoding are given to NMR signals by the gradient magnetic field, and the NMR signals are measured as time series data. The NMR signals are reconstructed as an image by a two-dimensional or three-dimensional Fourier transform. An operator sets a region to be imaged as an imaging slice through a GUI or the like. The imaging slice that the operator designates through a GUI or the like is converted into an imaging parameter, and the imaging of the imaging slice is performed. In addition, in this specification, an imaging region involving not only an imaging region at the time of single slice imaging but also a three-dimensional region at the time of multi-slice imaging is called an imaging slice hereinafter.

In an examination using an MRI apparatus, a cross-section that is anatomically determined is usually imaged for each part to be examined. This cross-section is called an examination section. In the examination, the operator sets this examination section as an imaging slice for each object. For example, in the case of medical checkup of the brain, as the examination section, there are planes along the reference lines, such as the OM (Orbit-Meatus) line or the AC-PC (Anterior Comisure-Posterior Comisure) line. For these reference lines, anatomical feature points are their references. An operator sets an imaging slice so as to pass through the feature point. In addition, as an examination using an MRI apparatus, there is a postoperative follow-up examination in which the same part of the same object is continuously imaged. In this case, the operator sets the same position of the object as an imaging slice in each examination.

The setting of an imaging slice is performed manually on scanogram images (scanogram images for positioning) in three directions that are acquired for positioning. However, depending on the part, the setting of an imaging slice should be performed in three-dimensional space. In addition, various conditions should be satisfied under various constraints. Therefore, the setting is difficult and requires skill. For this reason, the setting accuracy or the time taken for the setting differs depending on the operator. In particular, in a region (for example, a joint region) where the anatomical structure is complicated, the difference is large.

In order to solve the difficulty of imaging slice setting, a method of automating a part of the setting procedure has been proposed (for example, refer to NPL 1). NPL 1 discloses a technique of learning the pattern of an imaging slice setting executed by an operator and using it as slice plan setting information in the imaging slice setting. Here, on a 3D image obtained by performing 3D (three-dimensional) volume imaging, an imaging slice is calculated using the slice plan setting information.

In addition, there is a technique of automatically determining an imaging slice at the time of actual imaging on the basis of an imaging slice set in advance on a standard image (for example, refer to PTL 1).

CITATION LIST

Patent Literature

[PTL 1] JP-A-2005-125099

Non Patent Literature

[NPL 1] Kazuaki Nakata et al., "Experience of use of Smart Exam", Routine Clinical MRI 2007, Vol. 38, No. 14, P. 55-59, Industrial Development Organization

SUMMARY OF INVENTION

Technical Problem

According to the technique disclosed in NPL 1, it is necessary to register the slice plan setting information in advance for each facility. The slice plan setting information needs to be registered for multiple names, at least five people. In order to improve the accuracy of the set imaging slice, the larger number of registrations, the better. Therefore, in order to use the function with high positioning accuracy, time for preparatory work is very long. In addition, when the slice plan setting information needs to be changed, it is necessary to perform 3D volume imaging again. This takes time.

According to the technique disclosed in PTL 1, imaging for the above-described slice plan setting is not necessary. However, since the imaging position set on the standard image is one type set in advance, there is no degree of freedom for each facility. In addition, the accuracy of the set imaging position is also unknown.

The present invention has been made in view of the above-described situation, and it is an object of the present invention to provide an imaging slice setting technique capable of reducing the burden on the operator and having high accuracy and a high degree of freedom.

Solution to Problem

In the present invention, a standard imaging slice is registered in the system in advance, and a GUI allowing the operator to appropriately adjust the standard imaging slice is provided. The standard imaging slice is displayed on a standard image configured to include two-dimensional images in three directions similar to a positioning image, and can be adjusted on the image. At the time of main imaging, the standard image is fitted to the positioning image to specify an imaging slice on the positioning image.

Specifically, there is provided a medical imaging apparatus including: a standard imaging slice database in which a standard imaging slice is stored so as to match a standard image for each imaging part; display means for displaying the standard image and the standard imaging slice; operation receiving means for receiving an instruction to change the standard imaging slice displayed on the display means; and position update means for updating the standard imaging slice in the standard imaging slice database according to the received change instruction.

In addition, there is provided an imaging slice determination method including: a standard imaging slice display step of displaying a standard image and a standard imaging slice for each imaging part that are stored in advance; a change receiving step of receiving an instruction to change the standard imaging slice on the displayed standard image; a change step of changing the stored standard imaging slice according to the received change instruction; and an imaging slice determination step of determining, from a shape relationship between the standard image and a positioning image acquired for positioning, an imaging slice on the positioning image equivalent to the standard imaging slice.

Advantageous Effects of Invention

According to the present invention, it is possible to reduce the burden on the operator, and it is also possible to set an imaging slice with a high degree of freedom and with high accuracy.

BRIEF DESCRIPTION OF DRAWINGS

FIG. 4 is an explanatory view for describing an examination section database of the first embodiment.

FIG. 16 is a flowchart of another example of the standard imaging slice adjustment processing of the first and second embodiments.

DESCRIPTION OF EMBODIMENTS

<<First Embodiment>>

Figure 1:
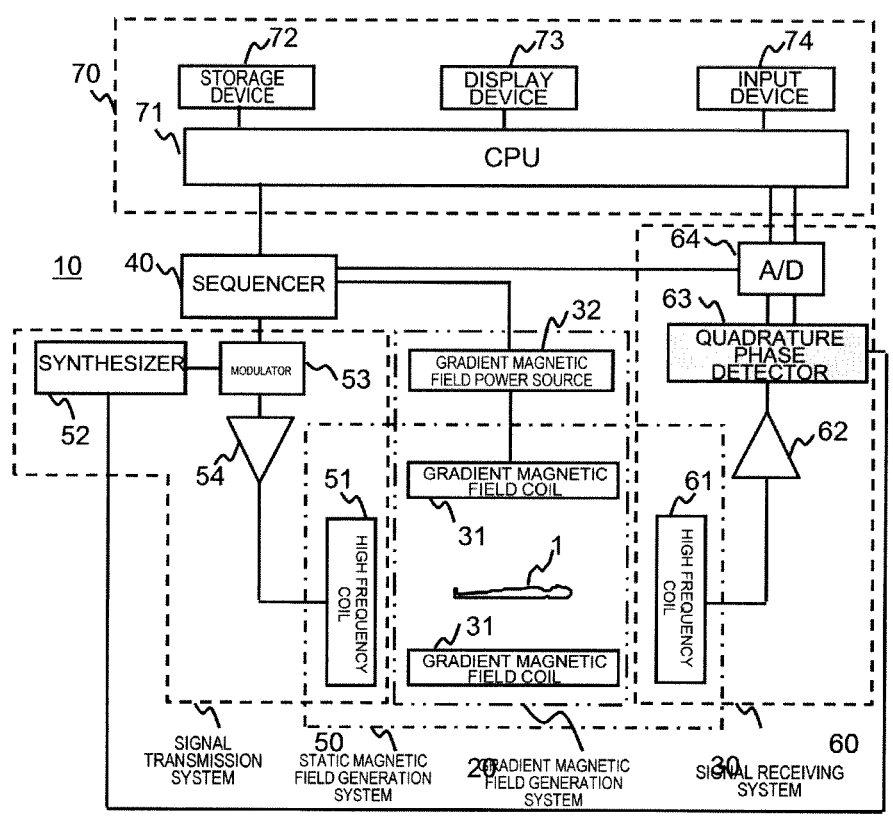
FIG. 1 is a block diagram showing the overall configuration of an MRI apparatus of a first embodiment.

Hereinafter, a first embodiment to which the present invention is applied will be described. Hereinafter, in all drawings for explaining the embodiments of the present invention, the same reference numerals are given to elements having the same functions, and repeated explanation thereof will be omitted.

First, the outline of an example of the MRI apparatus of the present embodiment will be described. FIG. 1 is a block diagram showing the overall configuration of an MRI apparatus 10 of the present embodiment. The MRI apparatus 10 of the present embodiment acquires a tomographic image of an object using an NMR phenomenon. As shown in FIG. 1, the MRI apparatus 10 includes a static magnetic field generation system 20, a gradient magnetic field generation system 30, a signal transmission system 50, a signal receiving system 60, a control processing system 70, and a sequencer 40.

The static magnetic field generation system 20 generates a uniform static magnetic field in a surrounding space of an object 1 in a direction perpendicular to the body axis in the case of a vertical magnetic field method and in the body axis direction in the case of a horizontal magnetic field method, and includes a permanent magnet type, normal conduction type, or superconducting type static magnetic field generator disposed around the object 1.

The gradient magnetic field generation system 30 includes gradient magnetic field coils 31 wound in three axial directions of X, Y, and Z, which are the coordinate system (stationary coordinate system) of the MRI apparatus 10, and a gradient magnetic field power source 32 which drives each gradient magnetic field coil, and applies gradient magnetic fields Gx, Gy, and Gz in the three axial directions of X, Y, and Z by driving the gradient magnetic field power source 32 of each gradient magnetic field coil 31 according to a command from the sequencer 4, which will be described later.

The signal transmission system 50 emits a high frequency magnetic field pulse (hereinafter, referred to as an "RF pulse") to the object 1 in order to cause nuclear magnetic resonance in the nuclear spins of atoms which form the body tissue of the object 1, and includes a high frequency oscillator (synthesizer) 52, a modulator 53, a high frequency amplifier 54, and a transmission-side high frequency coil (transmission coil) 51. The high frequency oscillator 52 generates an RF pulse and outputs it at the timing based on a command from the sequencer 40. The modulator 53 performs amplitude modulation of the output RF pulse, and the high frequency amplifier 54 amplifies the amplitude-modulated RF pulse and supplies it to the transmission coil 51 disposed near the object 1. The transmission coil 51 emits the supplied RF pulse to the object 1.

The signal receiving system 60 detects a nuclear magnetic resonance signal (an echo signal, an NMR signal) emitted by the nuclear magnetic resonance of the nuclear spins, which form the body tissue of the object 1, and includes a receiving-side high frequency coil (receiving coil) 61, a signal amplifier 62, a quadrature phase detector 63, and an A/D converter 64. The receiving coil 61 is disposed near the object 1, and detects an NMR signal of the response of the object 1 induced by the electromagnetic wave emitted from the transmission coil 51. The detected NMR signal is amplified by the signal amplifier 62 and is then divided into two orthogonal signals by the quadrature phase detector 63 at the timing based on the command from the sequencer 40. Each of the orthogonal signals is converted into the digital amount by the A/D converter 64 and is transmitted to a signal processing system 70.

The sequencer 40 applies an RF pulse and a gradient magnetic field pulse repeatedly according to the predetermined pulse sequence. In addition, the pulse sequence describes the timing or the strength of a high frequency magnetic field, a gradient magnetic field, and signal reception, and is stored in advance in the control processing system 70. The sequencer 40 operates according to the instruction from the control processing system 70, and transmits various commands, which are required for data collection of a tomographic image of the object 1, to the signal transmission system 50, the gradient magnetic field generation system 30, and the signal receiving system 60.

The control processing system 70 performs overall control of the MRI apparatus 10, various kinds of data processing, display and storage of processing results, and the like, and includes a CPU 71, a storage device 72, a display device 73, and an input device 74. The storage device 72 is formed by an external storage device, such as a hard disk, an optical disc, and a magnetic disk. The display device 73 is a CRT or a liquid crystal display device. The input device 74 is an interface for the input of various kinds of control information of the MRI apparatus 10 or control information of processing performed in the control processing system 70. For example, the input device 74 includes a track ball or a mouse and a keyboard. The input device 74 is disposed near the display device 73. The operator interactively inputs instructions and data, which are required for various kinds of processing of the MRI apparatus 10, through the input device 74 while observing the display device 73.

The CPU 71 realizes the control of the operation of the MRI apparatus 10 and each processing, such as various kinds of data processing, of the control processing system 70 by executing a program stored in advance in the storage device 72 according to the instruction input by the operator. For example, when the data from the signal receiving system 60 is input to the control processing system 70, the CPU 71 executes processing, such as signal processing and image reconstruction, and displays a tomographic image of the object 1, which is the result, on the display device 73 and also records it in the storage device 72.

The transmission coil 51 and the gradient magnetic field coil 31 are provided in the static magnetic field space of the static magnetic field generation system 20, in which the object 1 is inserted, so as to face the object 1 in the case of a vertical magnetic field method and so as to surround the object 1 in the case of a horizontal magnetic field method. In addition, the receiving coil 61 is provided so as to face or surround the object 1.

Currently, a nuclide imaged by an MRI apparatus, which is widely used clinically, is a hydrogen nucleus (proton) which is a main constituent material of the object 1. In the MRI apparatus 10, the shapes or functions of the head, abdomen, limbs, and the like of the human body are imaged in a two-dimensional or three-dimensional manner by performing imaging of the spatial distribution of the proton density or the information regarding the spatial distribution of the relaxation time of the excited state.

The imaging procedure of the MRI apparatus 10 is as follows. First, an instruction is output to the signal transmission system 50 according to the pulse sequence, and an RF pulse is emitted from the transmission coil 51 to the object 1. To the echo signal generated from the object 1 in this manner, a different phase encoding is given according to the gradient magnetic field. As the number of phase encodings, a value of 128, 256, 512, or the like per image is usually selected. The receiving coil 61 detects each echo signal. The echo signal is usually detected as a time-series signal of 128, 256, 512, or 1024 sampling data items. These data items are transmitted from the signal receiving system 60 to the control processing system 70. Then, image processing, such as a two-dimensional Fourier transform, is performed in the control processing system 70. As a result, one reconstructed image is generated.

The position of an imaging slice, which is a region to be imaged, is determined by the slice selection gradient magnetic field and the radiation frequency of the RE pulse. In addition, the position information of the imaging slice is given to the reconstructed image captured by the MRI apparatus 10 of the present embodiment. The position information is expressed in a coordinate system (referred to as apparatus coordinates) set in advance for the MRI apparatus 10, for example.

Figure 2:
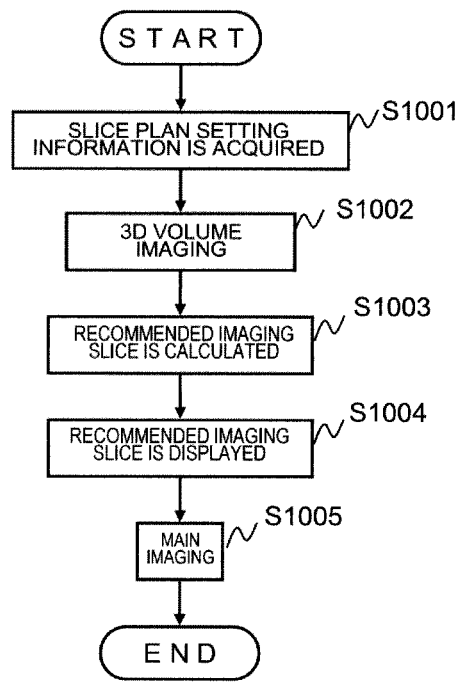
FIG. 2 is a flowchart of the imaging procedure in the related art.

Prior to the description of the imaging procedure including the imaging slice setting of the present embodiment, an imaging procedure in the related art will be described first. Here, using FIG. 2, the procedure disclosed in NPL 1 will be described as an example.

When an instruction to start the examination is received, slice plan setting information is acquired (step S1001). Here, for the examination section to be examined, imaging slices in a plurality of objects are set and registered. Then, 3D volume imaging for automatic positioning of imaging slices is performed (step S1002). Using the slice plan setting information and the 3D volume data acquired by 3D volume imaging, a recommended imaging slice that is recommended as an imaging slice for main imaging is calculated (step S1003), and the obtained recommended imaging slice is displayed (step S1004). Then, the recommended imaging slice is reflected in the imaging parameter, and main imaging is performed (step S1005).

Thus, if the technique disclosed in NPL 1 is used, it is possible to set the imaging slice without depending on the skill of the operator. In addition, the imaging slice that is set reflects the preference and trend of each facility. However, the slice plan setting information that is the basis for setting needs to be prepared for each facility.

Figure 3:
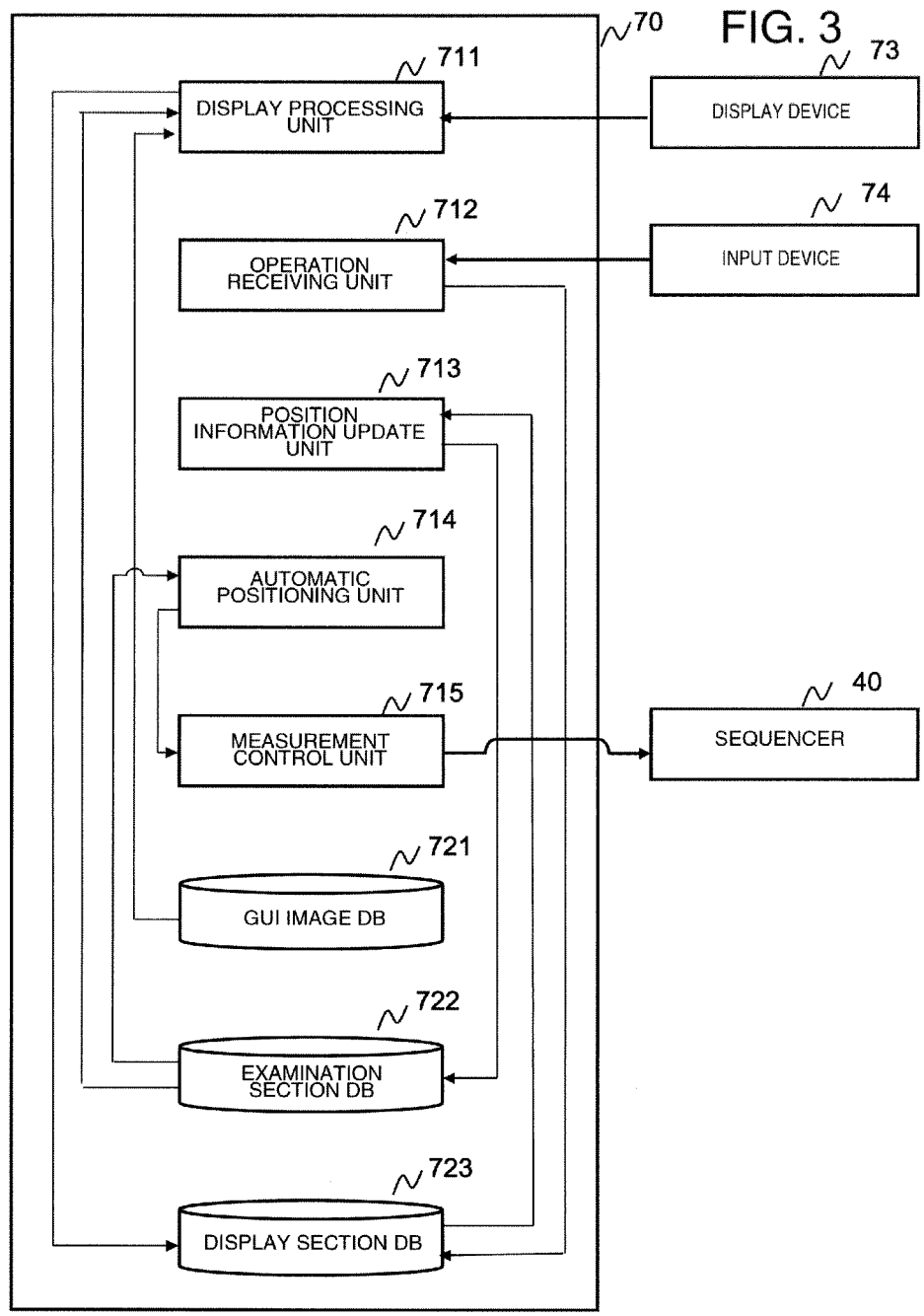
FIG. 3 is a functional block diagram of a control processing system of the first embodiment.

The MRI apparatus 10 of the present embodiment sets and stores an imaging slice, which is equivalent to the examination section, on a standard image, and also provides a GUI through which the imaging slice can be adjusted for each facility. In order to realize this, as shown in FIG. 3, the control processing system 70 of the MRI apparatus 10 of the present embodiment includes a display processing unit 711, an operation receiving unit 712, a position information update unit 713, an automatic positioning unit 714, a measurement control unit 715, a GUI (Graphical User Interface) image database (DB) 721, an examination section database (DB) 722, and a display section database (DB) 723.

Each database is stored in advance in the storage device 72. In addition, each function is realized when the CPU 71 loads a program stored in the storage device 72 to the memory and executes it.

The examination section DB 722 is a database in which information of the imaging slice (standard imaging slice) preset in the MRI apparatus 10 is stored. As shown in FIG. 4, in the examination section DB 722, a standard image 320 and an examination section 330 are registered for each examination part 310. For an examination part having a plurality of examination sections, the plurality of examination sections is registered. In addition, standard imaging slice position information 340, an operation section 350, and operating point position information 360 are registered in each examination section 330.

The examination part 310 is a part name that is an object to be examined in the examination routine. Here, for example, the brain, lumbar, knee, shoulder, and the like are registered.

The standard image 320 is standard two-dimensional images (a sagittal image, an axial image, and a coronal image) of each examination part, which is created in advance, in three directions. For example, an image created from the standard anatomical drawing of the organ that has been published or an image created by statistically processing (for example, averaging) images of a plurality of objects collected in advance is registered. The registered standard image may be a single slice image or may be a multi-slice image.

The examination section 330 is the name of the examination section (region) that is set in advance anatomically for each examination part 310. Here, the name of the examination section or the name of the specific reference line, which defines the examination section, is registered. For example, when the examination part is a brain, a plane along the OM (Orbit-Meatus) line or the AC-PC (Anterior Comisure-Posterior Comisure) line is the examination section. In this case, names, such as the OM line and the AC-PC line, are registered. In addition, names to be registered are not limited to such standard names, and a name unique for each facility may be registered.

The standard imaging slice position information 340 is the position information of the imaging position (imaging slice) of each examination section set on the standard image. Here, coordinate values in the coordinate system defined on the standard image are registered as the position information. The registered position information is a projection of each of the two-dimensional images in three directions onto the corresponding image. The initial value is registered in advance at the time of shipment.

The operation section 350 is the name of cross-sectional image for which an operation to change the position of a standard imaging slice is performed, among images of the three cross-sections registered in the standard image 320. According to the examination part 310 and the examination section 330, an optimal image is registered in advance. For example, when the examination part 310 is the brain and the examination section 330 is a region including the cerebellum and the cerebrum along the AC-PC line, a sagittal image is registered.

The operating point position information 360 is the position information of an operating point. The operating point is an operation tool for rotation and parallel movement of a standard imaging slice on the operation section 350 of the standard image 320, and includes a marking point for rotation operation and a central point for parallel movement operation. As the operating point position information 360, coordinates of the marking point and the central point on the operation section 350 of the standard image 320 are registered. The central point is a point indicating the center of an imaging region specified by the standard imaging slice on the operation section 350. The marking point is two points indicating the inclination of the standard imaging slice, and an anatomical feature point that defines the examination section and the like are used.

Data for generating the GUI screen supplied from the MRI apparatus 10 is stored in the GUI image DB 721. In the present embodiment, for example, data for generating GUI screens, such as an imaging condition setting screen and a standard imaging slice adjustment screen to be described later, is stored.

The display section DB 723 is a database in which operation target data is temporarily stored while the operator operates the standard imaging slice. As storage items, there are the examination part 310, the examination section 330, the standard imaging slice position information 340, and the operating point position information 360. The standard imaging slice position information 340 and the operating point position information 360 are changed whenever the standard imaging slice is moved by the instruction from the operator.

The display processing unit 711 controls the display of the display device 73 according to the instruction from the operator. In the present embodiment, a display image is generated by extracting the information from the GUI image DB 721, the examination section DB 722, and the display section DB 723, and it is displayed on the display device 73.

For example, when an instruction to start imaging condition setting is received from the operator, the display processing unit 711 extracts GUI image data for the generation of an imaging condition setting screen from the GUI image DB 721, generates the imaging condition setting screen, and displays it on the display device 73.

Figure 5:
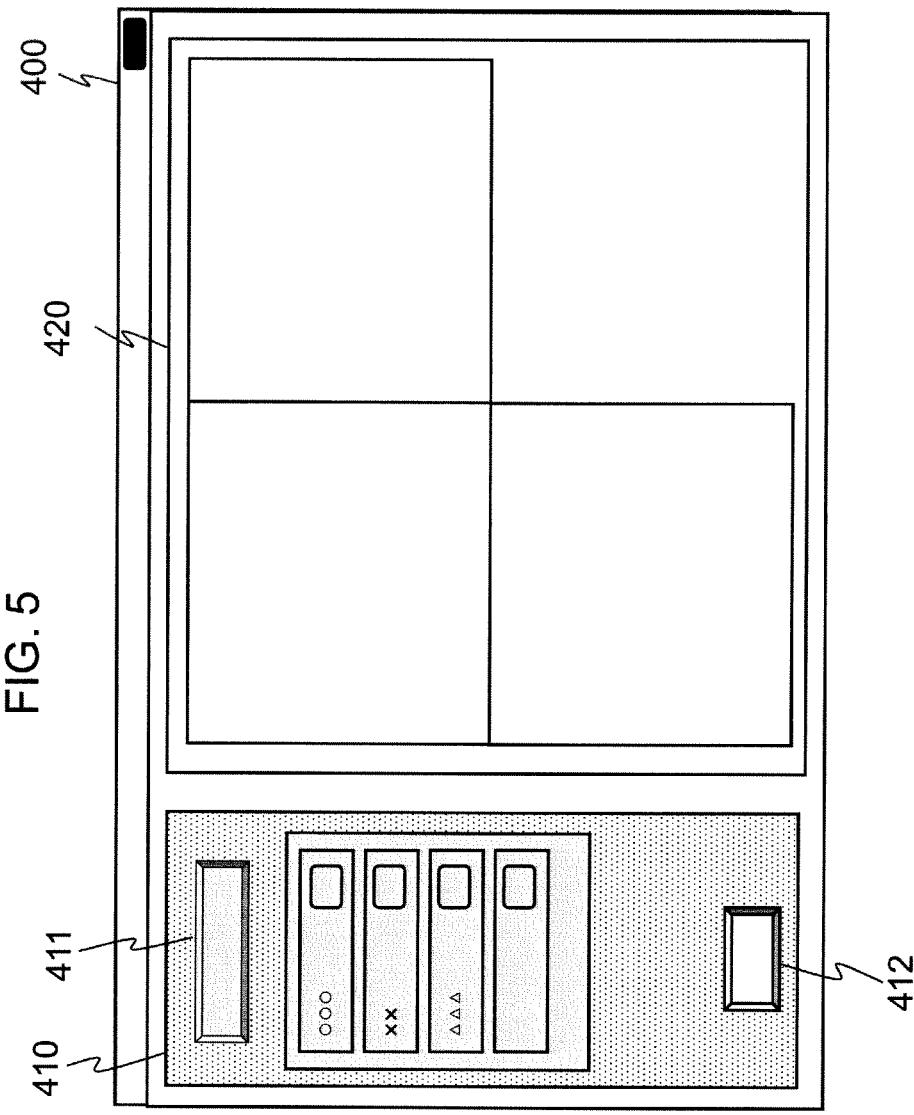
FIG. 5 is an explanatory view showing an example of the imaging condition setting screen of the first embodiment.

In this case, an example of the imaging condition setting screen of the present embodiment displayed by the display processing unit 711 is shown in FIG. 5. The imaging condition setting screen is a GUI that receives the setting of various kinds of imaging conditions. Here, the setting of an imaging slice is received. As shown in this drawing, an imaging condition setting screen 400 of the present embodiment includes an operating button display region 410 and an image display region 420 where two-dimensional images (an axial image, a sagittal image, and a coronal image) in three directions are displayed. The operating button region 410 includes a slice adjustment button 411 for accepting the instruction to start standard imaging slice adjustment processing, which will be described later, and an imaging start button 412 for accepting the instruction to start imaging.

In addition, when an instruction is received to start standard imaging slice adjustment, which is given using the slice adjustment button 411 of an examination window screen 400, the display processing unit 711 extracts GUI image data for the generation of a standard imaging slice adjustment screen from the GUI image DB 721, generates the standard imaging slice adjustment screen, and displays it on the display device 73. The standard imaging slice adjustment screen is a screen that receives an operation to adjust the standard imaging slice.

Figure 6:
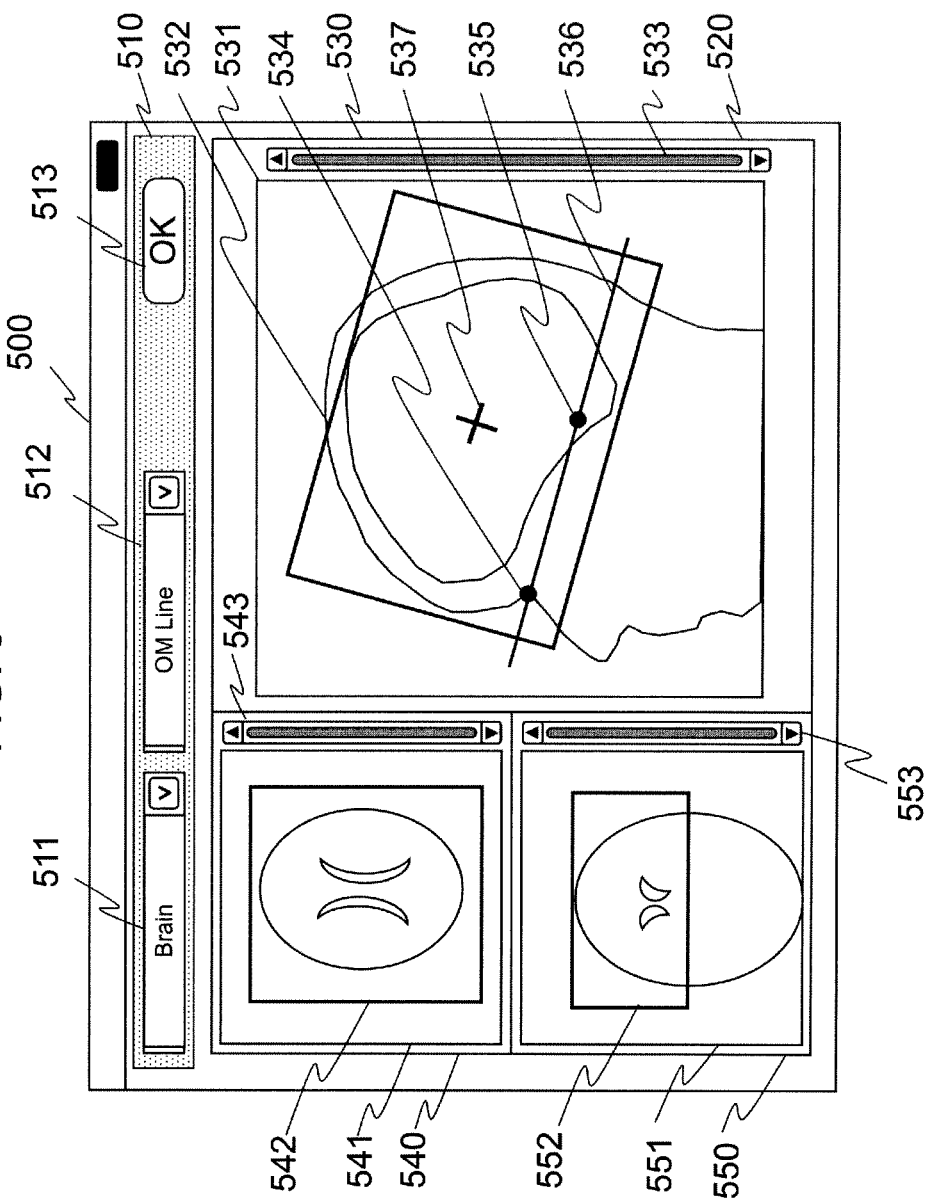
FIG. 6 is an explanatory view showing an example of the standard imaging slice adjustment screen of the first embodiment.

In this case, an example of the standard imaging slice adjustment screen displayed by the display processing unit 711 is shown in FIG. 6. As shown in this drawing, the standard imaging slice adjustment screen 500 includes an operating button display region 510 and an image display region 520.

The operating button region 510 includes a part selection column 511 for selecting a part of an image displayed on the image display region 520, a section selection column 512 for selecting the examination section, and an OK button 513 for accepting the intention to end the adjustment. Data stored in the examination part 310 of the examination section DB 722 is displayed in the part selection column 511, so that the selection of a part by the operator is accepted through the part selection column 511. In addition, data stored in the examination section name 330 of the examination section DB 722 is displayed in the section selection column 512, so that the selection of an examination section is accepted through the section selection column 512. In addition, although the display example based on the pull-down menu format using the part selection column 511 and the section selection column 512 as examples is shown herein, the display method is not limited thereto. A format in which a list and radio buttons are displayed, a check box format, and the like may also be used.

The OK button 513 accepts the instruction to end the adjustment from the operator. When the OK button 513 is pressed, the display processing unit 711 ends the display of the standard imaging slice adjustment screen 500 and displays the imaging condition setting screen 400.

The standard image 320 of the examination part 310 that is selected from the part selection column 511 by the operator is displayed in the image display region 520. The image display region 520 includes an operation section display region 530, a first section display region 540, and a second section display region 550. One different image, such as a sagittal image, an axial image, and a coronal image, of the standard image 320 is displayed in each display region. The operation section display region 530 is a region for receiving an operation to move a standard imaging slice on the cross-sectional image displayed in the display region. A cross-sectional image designated on the operation section 350 of the examination section DB 722 is displayed in the operation section display region 530. FIG. 6 illustrates a case where a sagittal image 531 is displayed in the operation section display region 530, an axial image 541 is displayed in the first section display region 540, and a coronal image 551 is displayed in the second section display region 550.

Moreover, in addition to the standard image 320, a standard imaging slice is displayed in each of the display regions 530, 540, and 550 according to the standard imaging slice position information 340 that is stored so as to match the examination section 330 selected from the examination section selection column 512 by the operator. In addition, in the operation section display region 530, an operating point is further displayed according to the operating point position information 360. A standard imaging slice is displayed on each image by markers 532, 542, and 552 indicating the standard imaging slice. The markers 532, 542, and 552 showing the standard imaging slice are projections of the standard imaging slice, which is seen from the R-L (left and right) direction, the H-F (body axis) direction, and the A-P (body thickness) direction, onto the image displayed in each display region. FIG. 6 illustrates a case where the plane along the OM line is selected as the examination section 330.

Two marking points 534 and 535 indicating the inclination (536) of the standard imaging slice and a central point 537 indicating the center of the projection of the standard imaging slice onto the cross-sectional image are displayed as operating points. In the present embodiment, an instruction to rotate the standard imaging slice (change the inclination) by the operation using the marking points 534 and 535 is received, and an instruction to move the standard imaging slice by the operation using the central point 537 is received. In addition, in the case of single slice imaging, the projection of the standard imaging slice to be set onto the standard image 320 is expressed in a straight line. Therefore, the central point 537 is disposed on a line 536 showing the inclination connecting the marking points 534 and 535.

In addition, scroll bars 533, 543, and 553 may be provided in the display regions 530, 540, and 550, respectively. When the standard image 320 stored in the examination section DB 722 is a multi-slice image, the change of the displayed slice is received through the operation using the scroll bars 533, 543, and 553. The operator can select a slice, in which the markers 532, 542, and 552 indicating the standard imaging slice are most easily seen, by operating the scroll bar.

When displaying the standard imaging slice adjustment screen 500, the display processing unit 711 displays the stored information of all examination parts 310 in the part selection column 511 with reference to the examination section DB 722 and receives the selection. Then, when an instruction from the operator regarding the examination part 310 is received through the part selection column 511, the display processing unit 711 displays all examination sections 330, which are stored so as to match the received examination parts 310, on the section selection column 512 with reference to the examination section DB 722. In addition, from the examination section DB 722, each cross-sectional image of the standard image 320 stored so as to match the examination part 310 is displayed on each of the display regions 530, 540, and 550 described above.

When the selection of the examination section 330 is received through the examination section selection column 512, the display processing unit 711 displays a cross-sectional image, which is designated on the operation section 350, on the operation section display region 530 and also displays the other two cross-sectional images on the first section display region 540 and the second section display region 550. In addition, the markers 532, 542, and 552 indicating the standard imaging slice are displayed in the display regions 530, 540, and 550 according to the standard imaging slice position information 340 that is stored in the examination section DB 722 so as to match the examination section 330, and the marking points 534 and 535 and the central point 537 are displayed on the cross-sectional image in the operation section display region 530 according to the operating point position information 360. In addition, the standard imaging slice position information 340 and the operating point position information 360 are stored in the display section DB 723 together with the examination part 310 and the examination section 330. The display processing unit 711 updates a display whenever the data in the display section DB 723 is updated thereafter.

The operation receiving unit 712 receives an operation using the operating point (the marking points 534 and 535 and the central point 537) of the standard imaging slice adjustment screen 500 and processes it. When an operation to rotate (change the inclination) and move (change the position) the standard imaging slice displayed on the standard imaging slice adjustment screen 500 is received, the operation receiving unit 712 monitors the amount of operation, calculates the position information of the operating points (the marking points 534 and 535 and the central point 537) and the standard imaging slice after the change and updates the information of the display section DB 723. Similar to the position information that specifies the imaging slice before the change, the calculated position information is a coordinate point when the coordinate system of the standard image is used.

The operation to change the inclination and the position is performed by clicking and drag-and-drop to the position after movement using a pointing device, instruction using operating buttons by which an instruction to move the specified operating point up and down and left and right can be given, and the like.

Figure 7:
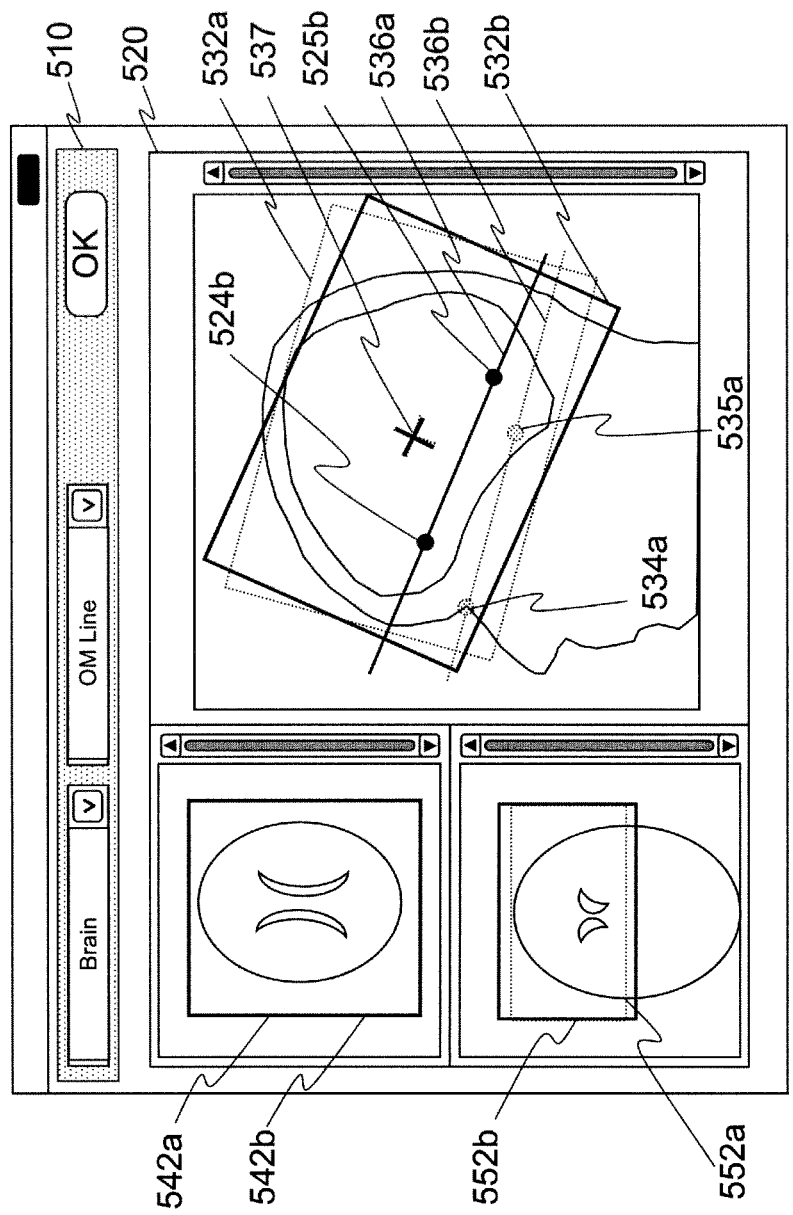
FIG. 7 is an explanatory view for describing the rotation operation on the standard imaging slice adjustment screen of the first embodiment.

FIG. 7 shows a state of the rotation operation. Here, marking points 534a and 535a before a change, a line 536a before a change that indicates the inclination, and markers 532a, 542a, and 552a before a change that indicate a standard imaging slice are shown by dotted lines, and these (534b, 535b, 536b, 532b, 542b, 552b) after the change are shown by the solid lines. As described above, the operator changes the inclination of the marker 532 indicating the standard imaging slice on the operation section by moving the marking points 534 and 535 to desired positions to change the inclination line 536 connecting both the marking points 534 and 535. The inclination changed on the operation section is also reflected in the markers 542 and 552 indicating the standard imaging slice on the other cross-sectional images. As shown in this drawing, in the case of a rotation instruction, there is no change in the position of the central point 537.

Figure 8:
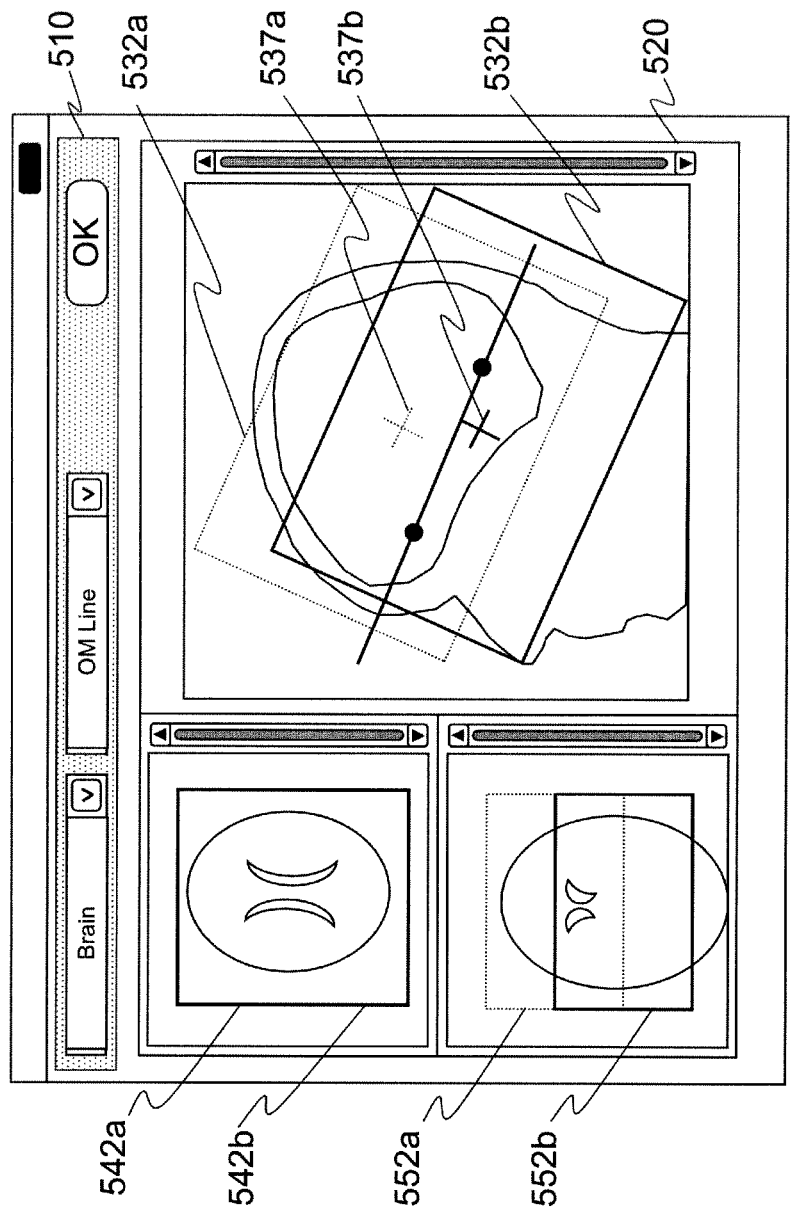
FIG. 8 is an explanatory view for describing the moving operation on the standard imaging slice adjustment screen of the first embodiment.

In addition, FIG. 8 shows a state of the parallel movement operation. Also in this drawing, a central point 537a before a change and markers 532a, 542a, and 552a before a change that indicate a standard imaging slice are shown by dotted lines, and these (537b, 532b, 542b, 552b) after the change are shown by the solid lines. The operator changes the position of the marker 532 indicating the standard imaging slice by moving the central point 537. The inclination changed on the operation section is also reflected in the markers 542 and 552 indicating the standard imaging slice on the other cross-sectional images.

Thus, by moving the marking points 534 and 535 and the central point 537, the operator can change the position and the inclination of the standard imaging slice so that a region that needs to be imaged in main imaging is included in the standard imaging slice.

The position information update unit 713 reflects the change of the standard imaging slice in the examination section DB. When an instruction of approval using the OK button 513 of the standard imaging slice adjustment screen 500 is received, the position information update unit 713 updates the standard imaging slice position information 340 and the operating point position information 360 of the examination section DB 722 with the information stored in the display section DB 723 at that point of time. Here, the standard imaging slice position information 340 and the operating point position information 360 of the data of the examination section DB 722 matching the examination part and the examination section of the display section DB 722 are replaced with the position information of the display section DB 723.

The automatic positioning unit 714 performs automatic positioning processing for setting an imaging slice, which is used in main imaging, on the positioning image on the basis of the standard imaging slice. When the imaging start button 412 is pressed, data corresponding to the examination section set in the imaging conditions is extracted from the examination section DB 722. Using this data, the automatic positioning processing is performed. The automatic positioning unit 714 determines an imaging slice on a positioning image by deforming (fitting) the standard image in the extracted data so as to match the positioning image while maintaining the relative position of the standard imaging slice with respect to the standard image. Here, the position information of the imaging slice based on the coordinate system defined on the positioning image is calculated, and an imaging parameter allowing the imaging at the position is calculated.

In addition, the positioning image is an image obtained by actually imaging an object. For the fitting, two-dimensional images (a sagittal image, a coronal image, and an axial image) in three directions at almost the same position as the standard image are used. In addition, the display processing unit 711 may be configured to display the determined imaging slice in the image display region 420 of the imaging condition setting screen 400 together with the positioning image.

When an imaging start instruction using the imaging start button 412 in the operating button region 410 of the imaging condition setting screen 400 is received, the measurement control unit 715 executes the imaging of the set imaging slice using the set imaging conditions and the designated pulse sequence.

Figure 9:
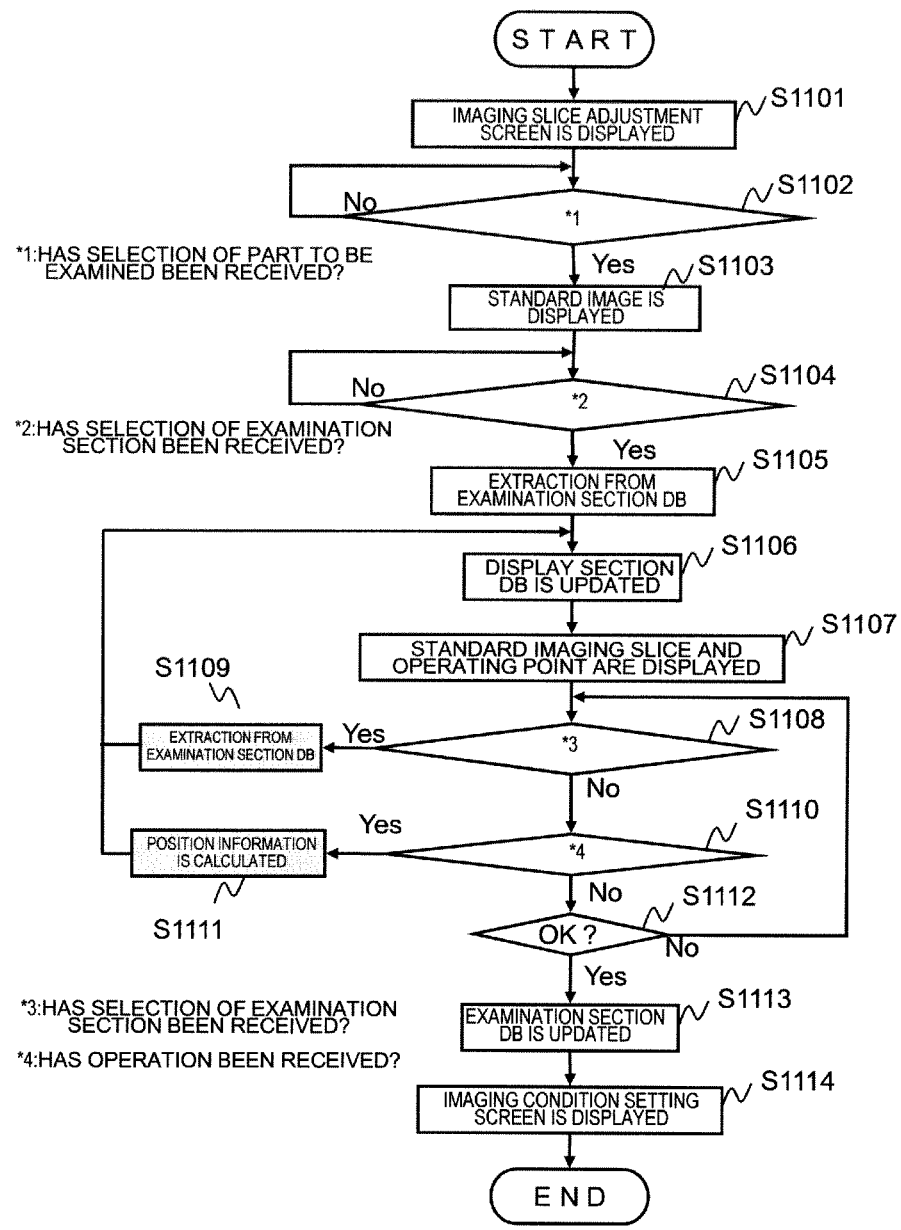
FIG. 9 is a flowchart of standard imaging slice adjustment processing of the first embodiment.

As described above, in the present embodiment, a standard imaging slice for each examination section that is stored in advance in the MRI apparatus 10 can be adjusted in each facility. Hereinafter, standard imaging slice adjustment processing which is this adjustment method will be described. FIG. 9 is a process flow of the standard imaging slice adjustment processing of the present embodiment.

When an instruction to start the standard imaging slice adjustment processing is received by pressing the slice adjustment button 411 displayed in the operating button region 410 of the imaging condition setting screen 400, the standard imaging slice adjustment processing is started. When a start instruction is received, the display processing unit 711 displays the standard imaging slice adjustment screen 500 (step S1101). In this case, since a part has not yet been selected, nothing is displayed in the image display region 510. In addition, for example, a standard image (for example, a head) and a standard imaging slice (for example, a region parallel to the AC-PC line) that are displayed as default may be set in advance, and this standard image and this standard imaging slice may be displayed.

Figure 10:
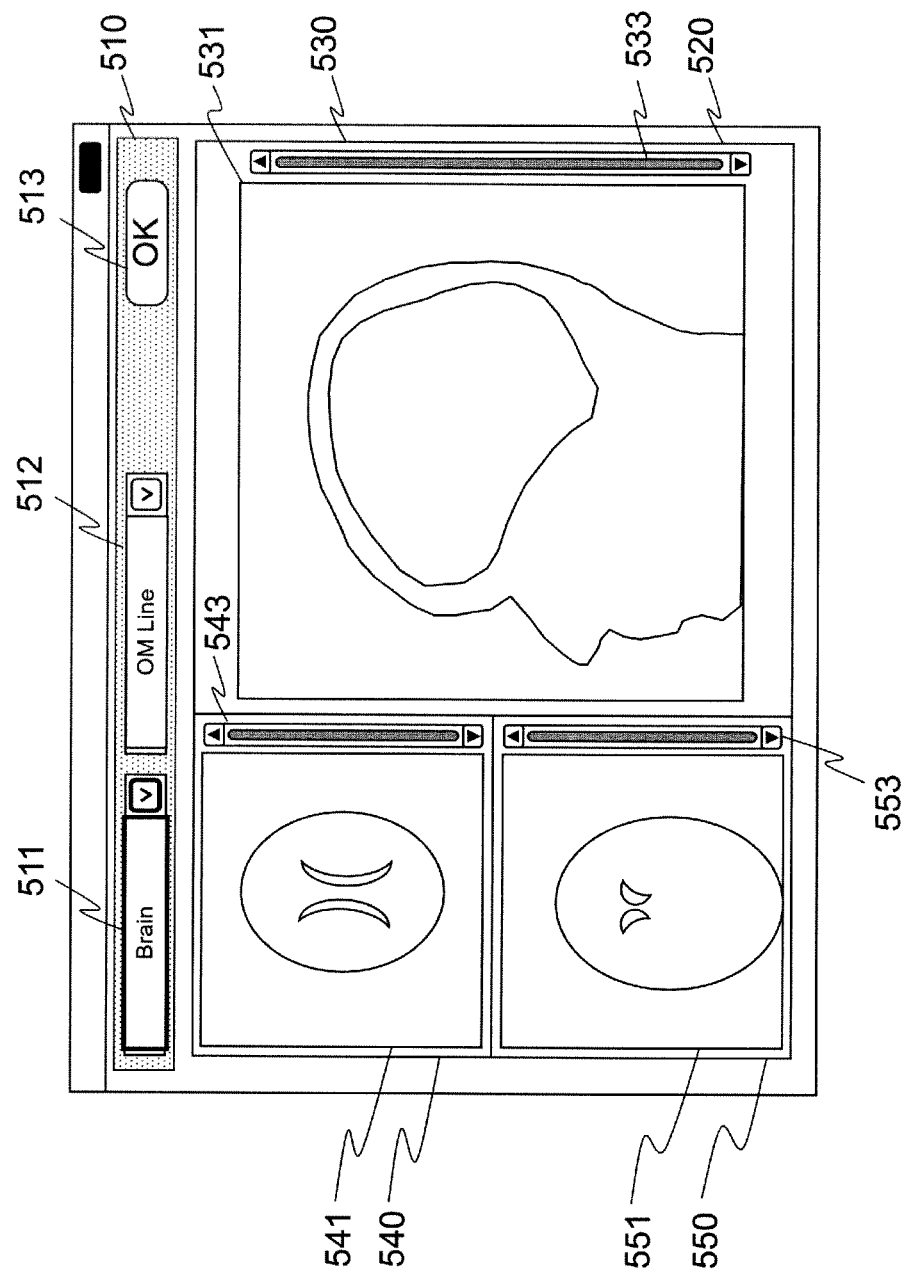
FIG. 10 is an explanatory view showing an example of the standard imaging slice adjustment screen of the first embodiment.

When the selection of an examination part to be adjusted is received through the part selection column 551 (step S1102), the display processing unit 711 extracts a standard image, which is stored so as to match the selected examination part 310, with reference to the examination section DB 722, and displays the sagittal image 531, the axial image 541, and the coronal image 551 in the image display region 520 (the operation section display region 530, the first section display region 540, and the second section display region 550) (step S1103). In addition, at this time, any cross-sectional image may be displayed in any display region. A screen example of the standard imaging slice adjustment screen displayed on the display device 73 at this time is shown in FIG. 10. Here, an example where the head is selected as the examination part 310 is shown.

Then, when the selection of an examination section to be adjusted is received through the section selection column 512 (step S1104), the display processing unit 711 extracts the standard imaging slice position information 340, the operation section 350, and the operating point position information 360, which are stored so as to match the selected examination section 330, with reference to the examination section DB 722 (step S1105). Then, the display section DB 723 is updated by registering both the examination part 310 and the examination section 330 in the display section DB 723 (step S1106).

Then, the display processing unit 711 displays the information registered in the display section DB 723 in the image display region 520 (step S1107). Here, the cross-sectional image designated on the operation section 350 is first displayed in the operation section display region 530. Then, other cross-sectional images are displayed in the first section display region 540 and the second section display region 550. In addition, the markers 532, 542, and 552 indicating the standard imaging slice are displayed on respective cross-sectional images (the sagittal image 531, the axial image 541, and the coronal image). An example of the screen displayed at this time is FIG. 6 described previously.

Here, the operator observes the markers 532, 542, and 552 indicating the standard imaging slice displayed on the standard imaging slice adjustment screen 500 to check whether or not a standard imaging slice of the desired examination section is displayed. Then, when it is determined that the standard imaging slice of the desired examination section is not displayed, the operator can select the examination section by pressing the section selection column 512 again.

Here, when the selection using the section selection column 552 is received (step S1108), the display processing unit 711 extracts the standard imaging slice position information 340, the operation section 350, and the operating point position information 360 that are stored in the examination section DB 722 so as to match the received examination section 330 (step S1109), and the process proceeds to step S1106 to repeat the process.

On the other hand, when the operation (rotation and/or parallel movement) to adjust the imaging slice position using the operating point on the cross-sectional image displayed in the operation section display region 530 is received (step S1110), the operation receiving unit 712 calculates the position information of the operating point and the standard imaging slice after the operation (step S1111). Then, the operation receiving unit 712 returns to step S1106 to update the display section DB 723 with the calculated position information. An example of the display screen at the time of adjustment operation is FIG. 7 or FIG. 8 described previously.

The display processing unit 711 and the operation receiving unit 712 repeat the process of steps S1106 to S1110 until the operator's instruction to end the adjustment, which is given through the OK button 513, is received (step S1112). When the OK button 513 is pressed, the position information update unit 713 updates the examination section DB 722 with the information registered in the display section DB 723 at that point of time (step S1113), thereby reflecting the adjustment result in the examination section DB 722. Then, the display processing unit 711 changes the display of the display device 73 to the imaging condition setting screen 400 (step S1114), and the process is ended.

By the processing described above, the MRI apparatus 10 of the present embodiment can adjust a standard imaging slice, which is prepared in advance, to an optimal standard imaging slice for each facility.

In addition, the standard imaging slice adjusted by the above-described processing may be used in all measurements using the MRI apparatus 10. In addition, a standard imaging slice may be adjusted for each examination task or each object in the above-described procedure, and may be registered together with a standard image so as to match each examination task or each object. In this case, for example, a new database in which the examination part 310, the standard image 320, the standard imaging slice position information 340, and the operating point 350 are stored for each examination task and each object is stored in the storage device 72 instead of updating the examination section DB 722 in step S1113, and the database is updated.

Figure 11:
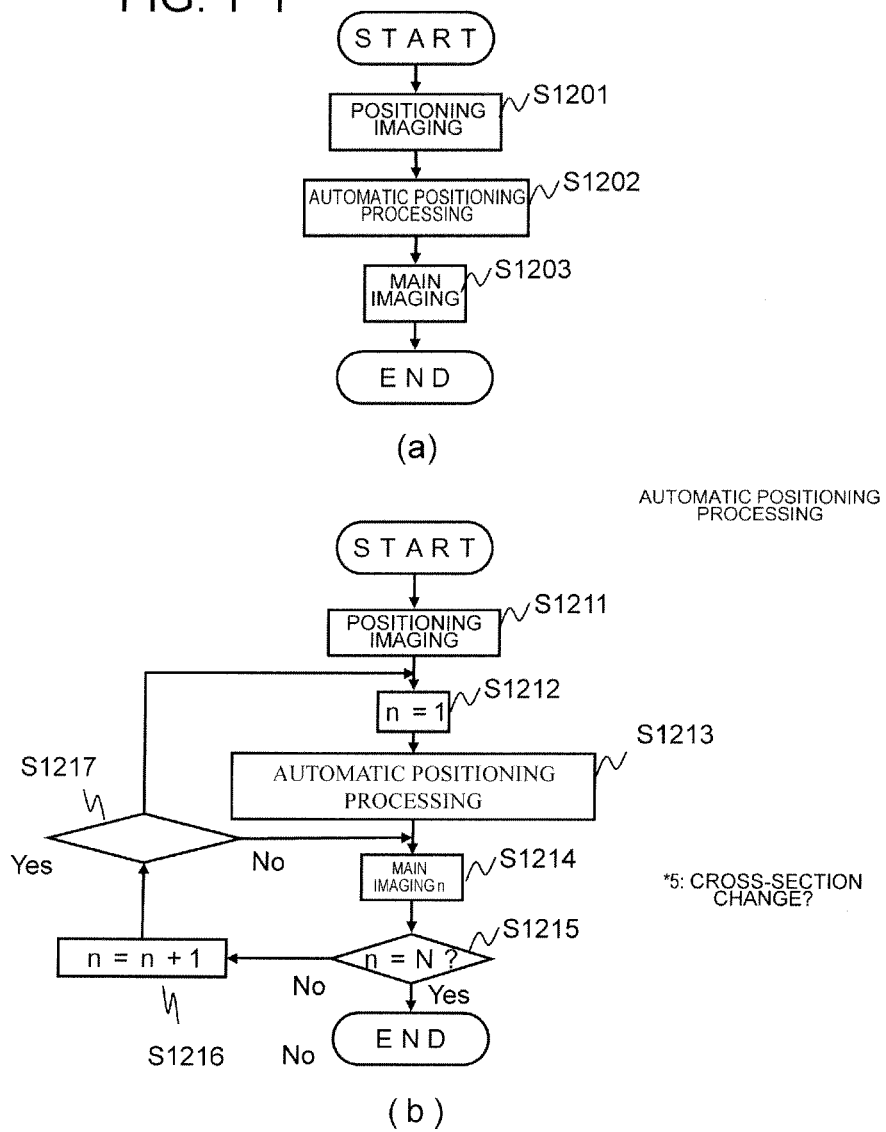
FIGS. 11(a) and 11(b) are flowcharts of the imaging procedure of the first embodiment.

Hereinafter, the flow of the process at the time of examination using the examination section DB 722 of the present embodiment will be described. FIG. 11A is the process flow of the present embodiment.

In the present embodiment, when the imaging conditions of those other than an imaging slice are set and an instruction to start imaging, which is given by the pressing of the imaging start button 412, is received, the measurement control unit 715 performs positioning imaging (step S1201). The positioning imaging is performed using the same method as in positioning imaging in the related art, thereby obtaining two-dimensional images (a sagittal image, an axial image, a coronal image) in three directions. Then, the automatic positioning unit 714 performs automatic positioning processing using the positioning image and the examination section DB 722 (step S1202). Then, the measurement control unit 715 executes main imaging of the imaging slice whose positioning has been done by the automatic positioning unit 714 (step S1203). After the positioning imaging (S1201), a scan for static magnetic field correction and the like is appropriately performed.

In addition, in the case of an examination protocol that continuously performs a plurality of imaging, the automatic positioning processing is performed whenever the examination section changes. In addition, the positioning imaging is performed once at the beginning of the examination protocol, and is not performed thereafter unless the arrangement of the object 1 is changed. Here, FIG. 11B shows the flow of the process at the time of execution of the examination protocol that executes N types of main imaging (each is expressed as main imaging n; N is a natural number, and n is a natural number satisfying n≤N).

As shown in this drawing, when an instruction to start imaging is received, the measurement control unit 715 performs positioning imaging as in FIG. 11A (step S1211). Then, the automatic positioning unit 714 performs automatic positioning processing using the positioning image and the examination section DB 722 (step S1213). Then, the measurement control unit 715 executes main imaging of the imaging slice whose positioning has been done by the automatic positioning unit 714 (step S1214). The measurement control unit 715 repeats the above processing until all imaging is ended. In this case, when the examination section of the next main imaging is the same as the examination section of the last main imaging, that is, when the examination section is not changed, the measurement control unit 715 returns to step S1214. When the examination section is different, the measurement control unit 715 returns to step S1213 (steps S1212, S1215, S1216, and S1217).

For example, an examination protocol that acquires three images of a T2-weighted image (first main imaging), a T1-weighted image (second main imaging), and a FLAIR image (third main imaging) on the first examination section, acquires a diffusion-weighted image (DWI: fourth main imaging) on the second examination section, and acquires an MRA image (fifth main imaging) on the third examination section is as follows. First, positioning imaging and automatic positioning processing are performed to execute the first main imaging, the second main imaging, and the third main imaging. Then, the automatic positioning processing is performed again to execute the fourth main imaging. Then, the positioning processing is performed again to execute the fifth main imaging.

As described above, according to the present embodiment, the MRI apparatus 10 has standard imaging slice information for each examination section. In addition, an imaging slice on the positioning image is automatically determined from the standard imaging slice. For this reason, the operator does not need to set the imaging slice manually for each examination. In addition, special measurement for standard imaging slice setting is not required, either. Therefore, high-accuracy imaging slice setting can be performed in a short time without depending on the skill of the operator. In addition, even when the same cross-section is continuously imaged, it is possible to set the imaging slice at the same position accurately.

In addition, according to the present embodiment, two-dimensional images in three directions that are similar to the positioning image are used for the GUI that adjusts a standard imaging slice. Therefore, the operator can adjust the standard imaging slice in the same sense as in the manual imaging slice setting for main imaging in the related art. As a result, it is possible to reduce difficulties in the operation.

In addition, the operation to adjust a standard imaging slice is easy. Accordingly, even if a default standard imaging slice is different from the imaging slice that is typically used in a facility, an optimal standard imaging slice for the facility can be acquired by changing the default standard imaging slice to the desired standard imaging slice easily. In addition, it is also possible to have a standard imaging slice adjusted for each examination task and each object. There are no restrictions on the standard imaging slice change timing. If a standard imaging slice is changed, the standard imaging slice after the change is automatically used thereafter. Therefore, according to the present embodiment, high-accuracy imaging slice setting can be realized with a high degree of freedom.

Therefore, according to the present embodiment, it is possible to reduce the burden on the operator, and it is also possible to set the imaging slice with high accuracy and with a high degree of freedom and perform imaging. Therefore, it is possible to acquire a high-quality image in a short time.

In addition, in the present embodiment, after adjusting the standard imaging slice, the position information update unit 713 necessarily reflects the adjustment received by the operation receiving unit 712. However, the present invention is not limited thereto. It is also possible to provide a CANCEL button, which is for accepting the intention to end the processing without reflecting the adjustment, on the standard imaging slice adjustment screen 500 and to end the processing without reflecting the adjustment result in the examination section DB 722 when the CANCEL button is pressed.

In addition, in the present embodiment, the automatic positioning unit 714 determines an imaging slice automatically from the standard imaging slice and executes the imaging as it is. However, the present invention is not limited thereto. The imaging slice determined by the automatic positioning unit 714 may be displayed first in the image display region 420 of the imaging condition setting screen 400, and the main imaging may be executed after obtaining the approval of the operator. In this case, the imaging slice may also be adjusted on the positioning image as in the related art.

Figure 12:
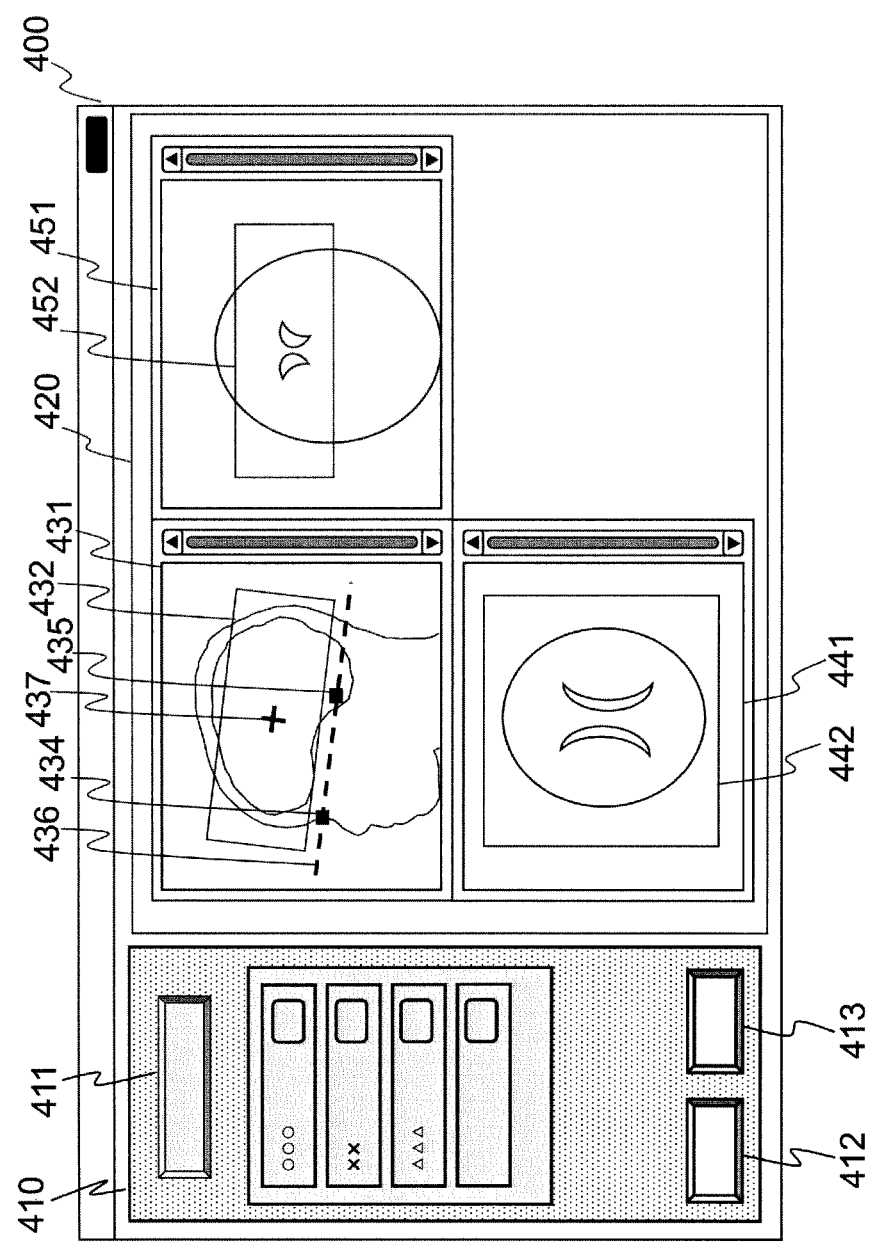
FIG. 12 is an explanatory view showing another example of the imaging condition setting screen of the first embodiment.

In addition, the automatic positioning unit 714 may calculate not only the imaging slice on the positioning image but also the point (second operating point) equivalent to the operating point and may display them simultaneously. A display example of the imaging condition setting screen 400 in this case is shown in FIG. 12. Here, a case where the operation section 350 is a sagittal image is illustrated.

A marker 432 indicating an imaging slice, marking points 434 and 435, a line 436 indicating the inclination, and a central point 437 are displayed in a sagittal image 431 of a positioning image. Markers 442 and 452 indicating imaging slices are displayed in an axial image 441 and a coronal image 451, respectively. The operator changes the position of an imaging slice by operating the operating point to perform rotation and parallel movement of the imaging slice.

<<Second Embodiment>>

Next, a second embodiment to which the present invention is applied will be described. In the present embodiment, a learning function of reflecting an imaging slice changed on a positioning image, which is obtained by actually imaging an object, on a standard imaging slice is provided. Basically, the MRI apparatus 10 of the present embodiment has the same configuration as in the first embodiment. The following explanation regarding the present embodiment will be focused on a different configuration from the first embodiment.

Figure 13:
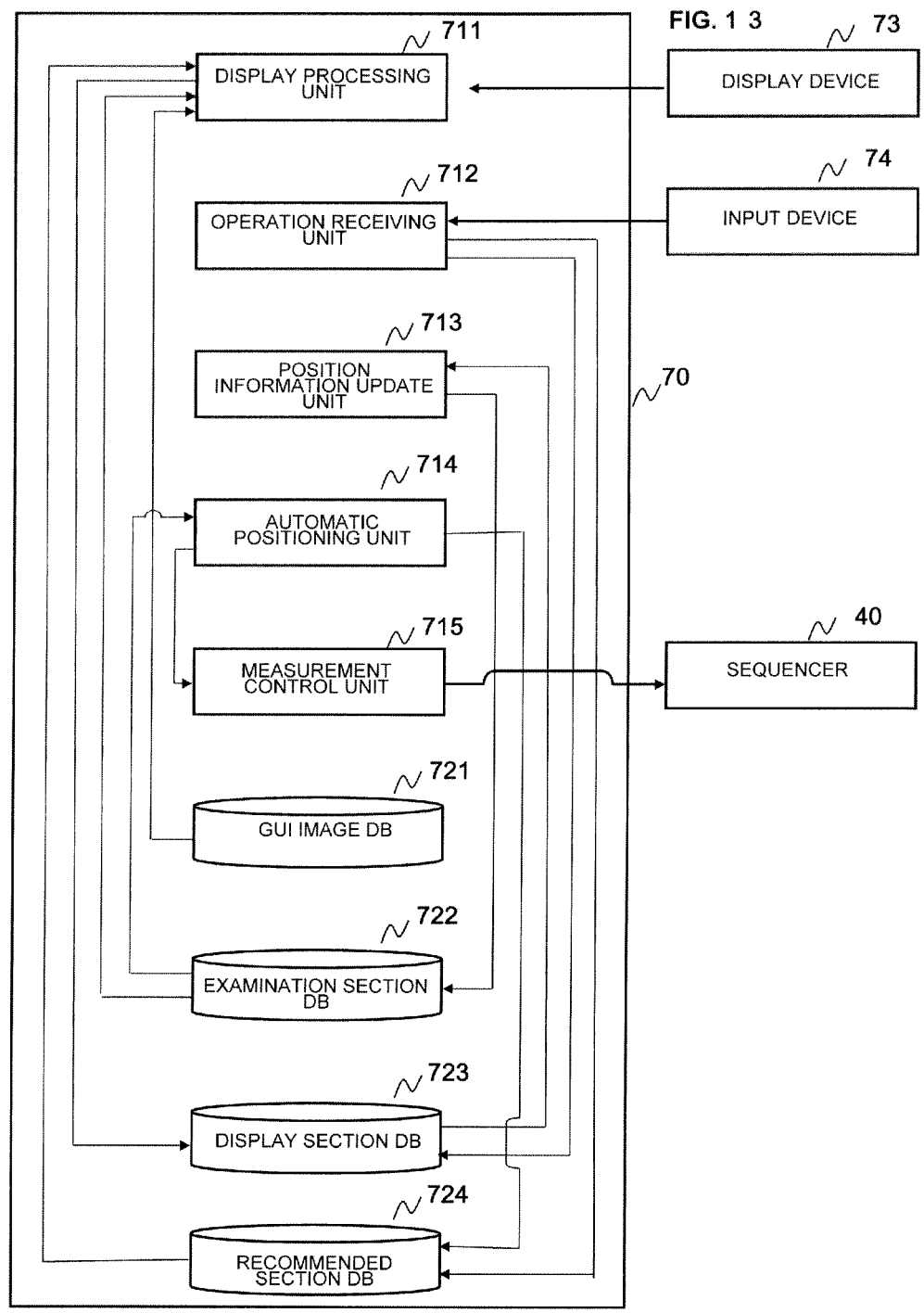
FIG. 13 is a functional block diagram of a control processing system of a second embodiment.

FIG. 13 is a functional block diagram of the control processing system 70 of the present embodiment. As shown in this drawing, in addition to the functions in the first embodiment, the control processing system 70 of the present embodiment includes a recommended section DB 724 in which data of the examination section DB 722 used when the automatic positioning unit 714 calculates an imaging slice of main imaging is temporarily stored. Hereinafter, a function of each unit will be described focusing on the differences from the first embodiment.

As in the first embodiment, when the examination section is designated, the automatic positioning unit 714 of the present embodiment calculates an imaging slice on a positioning image from a standard imaging slice. The imaging slice on the positioning image calculated by the automatic positioning unit 714 is called a recommended imaging slice in the present embodiment. In addition, when the calculated recommended imaging slice is approved through an OK button which will be described later, the automatic positioning unit 714 of the present embodiment sets the recommended imaging slice as an imaging slice of main imaging.

In addition, when predetermined conditions are satisfied, the automatic positioning unit 714 of the present embodiment reflects the adjustment of the recommended imaging slice on the positioning image in the standard imaging slice.

Specifically, when the examination section is designated and an instruction to start imaging is received, the automatic positioning unit 714 of the present embodiment extracts data, which corresponds to the examination section set in the imaging conditions, from the examination section DB 722 and registers the data in the recommended section DB 724. Information to be registered is the examination part 310, the standard image 320, the examination section 330, the standard imaging slice 340, the operation section 350, and the operating point 360.

In addition, the automatic positioning unit 714 of the present embodiment calculates the position information of the operating point on the positioning image. The calculation method is the same as the method of calculating the position information of an imaging slice that has been described in the first embodiment. In addition, the position information to be calculated is coordinate values in the coordinate system d on the positioning image, as in the first embodiment. In addition, in the present embodiment, the calculated operating point on the positioning image is called a second operating point. In addition, the automatic positioning unit 714 additionally registers the calculated recommended imaging slice position information and second operating point position information in the recommended section DB 724.

In addition, the automatic positioning unit 714 of the present embodiment performs adjustment reflection processing when an OK button, which will be described later, is pressed. The adjustment reflection processing is a processing for determining whether or not to register the recommended imaging slice at that time as a standard imaging slice and registering the recommended imaging slice according to the determination result. This determination is performed according to whether or not the amount of adjustment is within a predetermined range, and the recommended imaging slice is registered when it is determined that the amount of adjustment is in the predetermined range.

The calculation of the amount of adjustment is performed in the following procedure. First, a second standard imaging slice on the standard image, which is equivalent to the recommended imaging slice after the adjustment, is calculated. The calculation is performed in the reverse process of the process of calculating the recommended imaging slice from the standard imaging slice in the first embodiment. That is, for the position equivalent to the recommended imaging slice on the standard image deformed so as to match the positioning image, a position on the standard image before deformation is calculated, and this is set as a second standard imaging slice. In addition, in this case, the operating point on the standard image corresponding to the second operating point is similarly calculated. In addition, the amount of adjustment is determined by the comparison with the standard imaging slice registered in the recommended section DB 724.

In addition to the function described in the first embodiment, the display processing unit 711 of the present embodiment displays the second operating point and a marker indicating the calculated recommended imaging slice in the image display region 420 of the imaging condition setting screen 400 together with three cross-sections (a sagittal image, a coronal image, and an axial image) of each positioning image whenever the recommended section DB 724 is updated.

Figure 14:
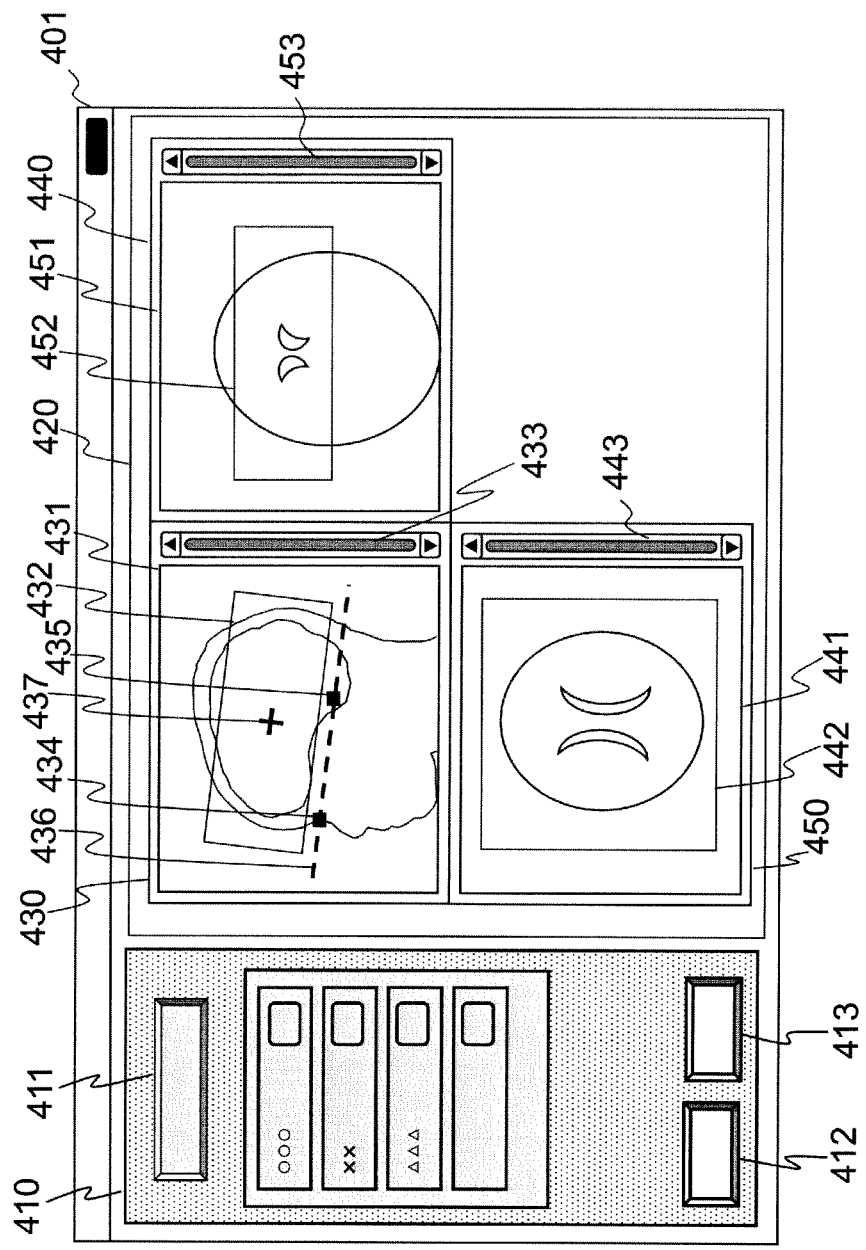
FIG. 14 is an explanatory view showing an example of the imaging condition setting screen of the second embodiment.

FIG. 14 shows an imaging condition setting screen 401 that the display processing unit 711 of the present embodiment displays.

Here, those having the same functions as the imaging condition setting screen 400 of the first embodiment are denoted by the same reference numerals. The image display region 420 of the imaging condition setting screen 401 of the present embodiment includes a first section display region 430, a second section display region 440, and a third section display region 450 in which three cross-sections of the positioning image are displayed. The display processing unit 711 displays each cross-sectional image of the positioning image in each display region and also displays the second operating point (marking points 434 and 435, a line 436 indicating the inclination, and a central point 437) and the marker (432, 442, and 452) indicating the recommended imaging slice on the positioning image in a direction designated as the operation section 350 of the standard image 320. In addition, scroll bars 433, 443, and 453 may be provided in the display regions 430, 440, and 450, respectively.

In addition, the imaging condition setting screen 401 of the present embodiment further includes an OK button 413 for accepting the intention to end the adjustment, that is, the intention to set the displayed recommended imaging slice as an imaging slice used in main imaging.

In addition to the function described in the first embodiment, the operation receiving unit 712 of the present embodiment receives an operation using the second operating point (marking points 434 and 435 and a central point 437) of the image display region 420. That is, the operation receiving unit 712 receives an operation to rotate a recommended imaging slice 432 using the marking points 434 and 435 and an operation to move the recommended imaging slice 432 using the central point 437. In addition, as in the first embodiment, when the operation is received, the operation receiving unit 712 monitors the amount of operation, calculates the position information of the recommended imaging slice after the change and the position information of the second operating point, and updates the recommended section DB 723 with the calculated position information. The calculated position information is assumed to be a coordinate point when, in the coordinate system of the positioning image is used, in the same manner as before the change.

In addition, the standard imaging slice adjustment processing of the present embodiment is the same as that in the first embodiment.

Figure 15:
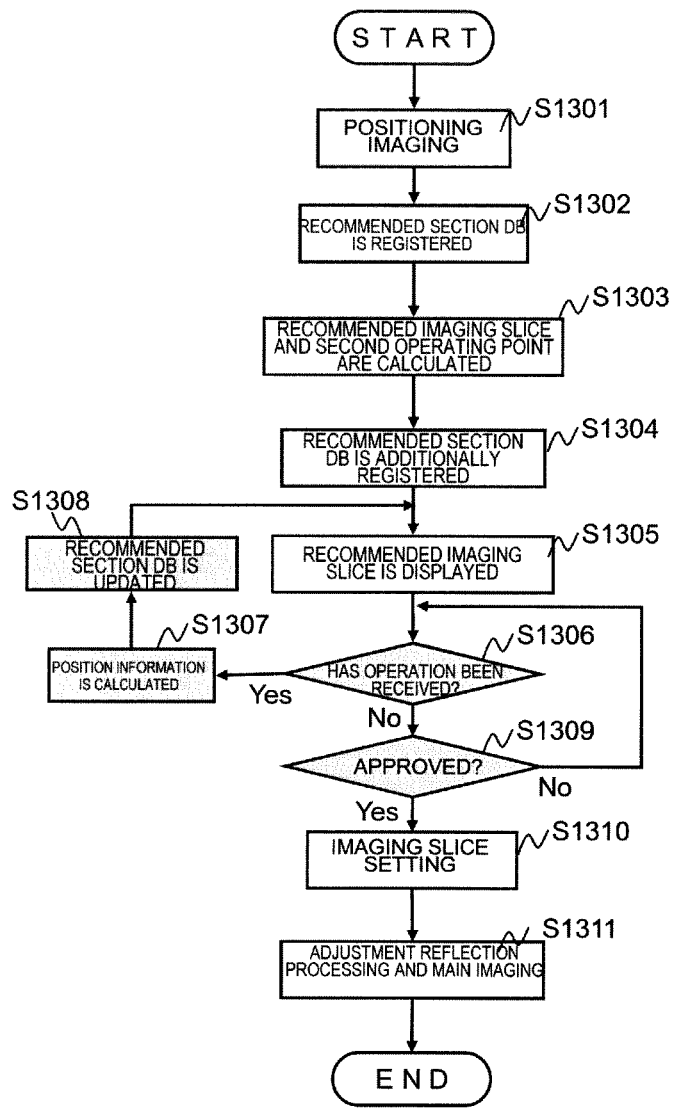
FIG. 15 is a flowchart of the imaging procedure of the second embodiment.

Next, the imaging procedure of the present embodiment will be described. FIG. 15 is a process flow of the imaging procedure of the present embodiment.

When an instruction to start imaging, which is given by the pressing of the imaging start button 412, is received, the measurement control unit 715 performs positioning imaging as in the first embodiment (step S1301). Then, the automatic positioning unit 714 registers the information of the examination section DB 722 regarding the examination section 330, which needs to be set, in the recommended section DB 724 (step S1302). Then, the recommended imaging slice and the second operating point are calculated using the positioning image and the recommended section DB 724 (step S1303). Then, such information is added to the recommended section DB 724 (step S1304).

The display processing unit 711 displays the recommended imaging slice and the second operating point, which are registered in the recommended section DB 724, on a positioning image of the cross-section registered in the recommended section DB 724 as the operation section of a standard image (step S1305).

When the operation (rotation and/or parallel movement) to adjust the position of the recommended imaging slice using the second operating point displayed in the image display region 420 is received (step S1306), the operation receiving unit 712 calculates the position information of the recommended imaging slice after the operation and the second operating point after the operation (step S1307). Then, the operation receiving unit 712 updates the recommended section DB 724 (step S1308), and proceeds to step S1305 to continue the process.

The display processing unit 711 and the operation receiving unit 712 repeat the process of steps S1303 to S1306 until the operator's intention to end the adjustment, which is given through the OK button 413, is received (step S1309). When the OK button 413 is pressed, the automatic positioning unit 714 sets the recommended imaging slice as an imaging slice (step S1310). Then, the automatic positioning unit 714 performs adjustment reflection processing, and the measurement control unit 715 executes main imaging of the imaging slice determined by the automatic positioning unit 714 (step S1311).

In addition, also in the present embodiment, in the case of an examination protocol that continuously performs a plurality of imaging, the automatic positioning processing is performed whenever the examination section changes, as in the first embodiment. In addition, the positioning imaging is performed once at the beginning of the examination protocol, and is not performed thereafter unless the arrangement of the object 1 is changed. That is, when the examination section of the next main imaging is the same as the examination section of the last main imaging, that is, when the examination section is not changed, the measurement control unit 715 performs the next main imaging. On the other hand, when the examination section of the next main imaging is different, the process returns to step S1302 to repeat the process.

As described above, according to the present embodiment, an imaging slice can be set accurately in a short time for each examination while securing a high degree of freedom without increasing the burden on the operator, as in the first embodiment. In addition, according to the present embodiment, adjustment of the imaging slice on the positioning image obtained by actually imaging the object is reflected in the standard imaging slice under predetermined conditions. Therefore, since it is possible to include a standard imaging slice of the position, which is more suitable for the actual conditions, the quality of the obtained image is further improved.

In addition, although whether or not to reflect the adjustment on the positioning image is determined according to the conditions set in advance in the present embodiment, the present invention is not limited thereto. For example, the operator may determine whether or not to reflect the adjustment.

In this case, for example, the imaging condition setting screen 400 includes a button for accepting an instruction of reflection. The automatic positioning unit 714 reflects an adjustment result according to the instruction of the operator. In addition, until the main imaging starts or an examination ends after step S1309 described above, the instruction of reflection may be received at any timing. That is, the automatic positioning unit 714 performs the above-described adjustment reflection processing to make the adjustment result on the positioning image reflected in the standard imaging slice only when the instruction of reflection is received during this period.

Moreover, in addition to the examination section DB 722 in which the standard imaging slice position used in the entire facility is stored, it is also possible to store the examination section DB 722 for each object, for example. In addition, the imaging slice position changed on the positioning image of the object may be reflected only in the examination section DB 722 for each object.

In addition, although the case where one cross-section (in the above example, a sagittal image) set in advance is an operation section has been described as an example in each embodiment, the operation section may be changed. In this case, in the examination section DB 722, the operating point position information 360 is stored in advance so as to match each cross-section. In addition, as the operation section 360 of the examination section DB 722, a cross-section that is an operation section in the initial state is stored.

The flow of standard imaging slice adjustment processing in this case will be described using FIG. 16. FIG. 16 is a process flow of the standard imaging slice adjustment processing. Also in this case, the process is started by the pressing of the slice adjustment button 411 displayed in the operating button region 410 of the imaging condition setting screen 400.

When an instruction to start the process is received, the display processing unit 711 displays the standard imaging slice adjustment screen 500 (step S1401). Then, when the selection of an examination part to be adjusted is received through the part selection column 551 (step S1402), the display processing unit 711 displays each cross-sectional image of the standard image, which is stored so as to match the selected examination part 310, in each of the display regions 530, 540, and 550 of the image display region 520 with reference to the examination section DB 722 (step S1403).

Then, when the selection of an examination section to be adjusted is received through the section selection column 512 (step S1404), the display processing unit 711 extracts the standard imaging slice 340, the operation section 350, and the operating point 360, which are stored so as to match the selected examination section 330, with reference to the examination section DB 722 (step S1405). Then, the display section DB 723 is updated by registering both the examination part 310 and the examination section 330 in the display section DB 723 (step S1406).

Then, the display processing unit 711 displays the information registered in the display section DB 723 in the image display region 510 (step S1407). Here, a cross-sectional image designated as an initial value on the operation section 350 is first displayed in the operation section display region 530. Then, other cross-sectional images are displayed in the first section display region 540 and the second section display region 550. In addition, the markers 532, 542, and 552 indicating the standard imaging slice and the operating point are displayed on respective cross-sectional images (the sagittal image 531, the axial image 541, and the coronal image 551).

Here, when the selection using the section selection column 552 is received (step S1408), the display processing unit 711 extracts the standard imaging slice 340, the operation section 350, and the operating point 360 that are stored in the examination section DB 722 so as to match the received examination section 330 (step S1409), and the process proceeds to step S1406 to repeat the process.

In addition, the operator can change the cross-sectional image, on which the standard imaging slice is adjusted, among the three cross-sectional images (the sagittal image 521, the coronal image 531, and the axial image 541) that are displayed. For example, a selection instruction is input by clicking a region where an image as the operation section is displayed. When the change instruction is received (step S1410), the display processing unit 711 changes the display by displaying the received cross-sectional image in the operation section display region 530 and displaying the other two cross-sections in the first other section display region 540 and the second other section display region 550 (step S1411).

In addition, when the operation (rotation and/or parallel movement) to adjust the imaging slice position using the operating point on the cross-sectional image displayed in the operation section display region 530 is received (step S1412), the operation receiving unit 712 calculates the position information of the operating point and the standard imaging slice after the operation (step S1413). Then, the operation receiving unit 712 returns to step S1406 to update the display section DB 723 with the calculated position information.

The display processing unit 711 and the operation receiving unit 712 repeat the process of steps S1406 to S1413 until the operator's instruction to end the adjustment, which is given through the OK button 513, is received (step S1414). When the OK button 513 is pressed, the position information update unit 713 updates the examination section DB 722 with the information registered in the display section DB 723 at that point of time (step S1415), thereby reflecting the adjustment result in the examination section DB 722. Then, the display processing unit 711 changes the display of the display device 73 to the imaging condition setting screen 400 (step S1416), and the process is ended.

In addition, the layout of the GUI screen illustrated in each embodiment is not limited thereto. Any kind of arrangement is possible as long as the regions and the buttons described in each embodiment are included.

In addition, although the inclination and the position of an imaging slice can be changed in each embodiment described above, the region size may also be changed further by increasing the number of operating points. In addition, the change of the region size may be performed by changing the imaging parameter. The imaging parameter may be calculated from parameters (slice thickness, a distance between slices, and the number of slices), which are relevant to the imaging region, among imaging parameters used in the examination. It is also possible to input directly a numerical value indicating the thickness of the imaging region.

In this case, the size of the imaging region set in the imaging conditions and the standard imaging slice can be approximately matched with each other. In addition, for the size of the imaging region, a setting stored as imaging conditions may be preferentially used without performing adjustment.

In addition, although the MRI apparatus has been described as an example in each of the above embodiments, the imaging slice setting method of each embodiment can be applied to a typical medical imaging apparatus that sets an imaging slice to perform imaging.

In addition, a medical imaging apparatus, such as the MRI apparatus 10, may not have each function of performing the standard imaging slice adjustment processing. Such a function may be realized on a separate information processing apparatus that can transmit and receive data to and from the MRI apparatus 10.

REFERENCE SIGNS LIST

10: MRI apparatus
20: static magnetic field generation system
30: gradient magnetic field generation system 31: gradient magnetic field coil
32: gradient magnetic field power source
40: sequencer
50: signal transmission system
51: transmission coil
52: high frequency oscillator
53: modulator
54: high frequency amplifier
60: signal receiving system
61: receiving coil
62: signal amplifier
63: quadrature phase detector
64: A/D converter
70: control processing system
71: CPU
72: storage device
73: display device
74: input device
310: examination part
320: standard image
330: examination section
340: standard imaging slice position information
350: operation section
360: operating point position information
400: imaging condition setting screen
410: operating button display region
411: slice adjustment button
412: imaging start button
413: OK button
420: image display region
430: first section display region
431: sagittal image
432: imaging slice marker
433: scroll bar
434: marking point
435: marking point
436: inclination line
437: central point
440: first section display region
441: axial image
442: imaging slice marker
443: scroll bar
450: first section display region
451: coronal image
452: imaging slice marker
453: scroll bar
500: standard imaging slice adjustment screen
510: operating button region
511: part selection column
512: section selection column
513: OK button
520: image display region
530: operation section display region
540: first section display region
550: second section display region
531: sagittal image
532: imaging slice marker
533: scroll bar
532*a*: imaging slice marker
532*b*: imaging slice marker
534: marking point
534*a*: marking point
534*b*: marking point
535: marking point
535*a*: marking point
535*b*: marking point
536: inclination line
536*a*: inclination line
536*b*: inclination line
537: central point
537*a*: central point
537*b*: central point
541: axial image
542: imaging slice marker
542*a*: imaging slice marker
542*b*: imaging slice marker
543: scroll bar
551: coronal image
552: imaging slice marker
552*a*: imaging slice marker
552*b*: imaging slice marker
553: scroll bar
711: display processing unit
712: operation receiving unit
713: position information update unit
714: automatic positioning unit
715: measurement control unit
721: GUI image DB
722: examination section DB
723: display section DB
724: recommended section DB

The invention claimed is:

1. A medical imaging apparatus comprising:
a standard imaging slice database in which a standard imaging slice is stored so as to match a standard image for each imaging part;
display means configured to display the standard image and the standard imaging slice;
operation receiving means configured to receive an instruction to change the standard imaging slice displayed on the display means;
standard imaging slice update means configured to update the standard imaging slice in the standard imaging slice database according to the received change instruction;
imaging slice determination means configured to determine, whenever a positioning image is acquired for positioning, an inmaging slice on the positioning image, which is equivalent to the standard imaging slice, from a shape relationship between the positioning image and the standard image,
wherein the display means displays the positioning image and the imaging slice,
the operation receiving means further receives a change of an imaging slice on the positioning image displayed on the display means, and
when a change amount by the change on the positioning image is within a predetermined range, the standard imaging slice update means reflects the change on the positioning image in the standard imaging slice in the standard imaging slice database; and
determination means configured to receive an instruction regarding whether to reflect the received change in the standard imaging slice database,
wherein the operation receiving means further receives a change of an imaging slice on the positioning image, and
the standard imaging slice update means reflects the change on the positioning image in the standard imaging slice in the standard imaging slice database when the determination means receives an instruction to reflect the received change.

2. The medical imaging apparatus according to claim 1,
wherein the standard imaging slice on the standard image includes a plurality of marking points for specifying an inclination of the standard imaging slice on the standard image, and
the operation receiving means receives an operation on the marking point as an instruction to change the inclination of the standard imaging slice.

3. The medical imaging apparatus according to claim 1,
wherein the standard imaging slice on the standard image includes a central point indicating the center of an imaging slice, and
the operation receiving means receives an operation on the central point as an instruction to move the standard imaging slice.

4. The medical imaging apparatus according to claim 1,
wherein the standard image includes an axial image, a coronal image, and a sagittal image.

5. The medical imaging apparatus according to claim 4,
wherein the operation receiving means receives an instruction of the change on the sagittal image.

6. The medical imaging apparatus according to claim 1,
wherein the standard image is an image obtained by statistically processing a plurality of existing images, and
the standard imaging slice is a cross-sectional position, which is anatomically set in advance, on the standard image.

7. The medical imaging apparatus according to claim 1,
wherein the medical imaging apparatus is a magnetic resonance imaging apparatus.

8. An imaging slice determination method comprising:
a standard imaging slice display step of displaying a standard image and a standard imaging slice for each imaging part that are stored in advance;
a change receiving step of receiving an instruction to change the standard imaging slice on the displayed standard image;
a change step of changing the stored standard imaging slice according to the received change instruction;
an imaging slice determination step of determining, from a shape relationship between the standard image and a positioning image acquired for positioning, an imaging slice on the positioning image equivalent to the standard imaging slice;
a second chance of receiving step of receiving an instruction to change the determined imaging slice on the positioning image; and
a change reflection step of reflecting the received imaging slice than in the standard imaging slice according to an instruction from an operator or a reference set in advance.

9. A medical imaging apparatus comprising:
a standard imaging slice database in which a standard imaging slice is stored so as to match a standard image for each imaging part;
a processor configured to determine an imaging slice;
a display device configured to display a positioning image and the imaging slice; and
an operation receiving device configured to receive a change of the imaging slice on the positioning image displayed on the display device and an instruction regarding whether to reflect the change in the standard imaging slice database,
wherein the processor is further configured to perform functions including:
determining, whenever the positioning image is acquired for positioning, the imaging slice on the positioning image, which is equivalent to the standard imaging slice, from a shape relationship between the positioning image and the standard image; and
reflecting the change of the imaging slice on the positioning image in the standard imaging slice in the standard imaging slice database according to the received instruction to reflect the change in the standard imaging slice database.

* * * * *